(12) United States Patent
Hasson et al.

(10) Patent No.: US 10,336,817 B2
(45) Date of Patent: Jul. 2, 2019

(54) THERAPEUTIC COMPOSITION OF CAMEL MILK

(71) Applicant: SULTAN QABOOS UNIVERSITY, Al-Khodh (OM)

(72) Inventors: Sidgi Syed Anwer Abdo Hasson, Al-Khodh (OM); Ali A. H. Al-Jabri, Al-Khodh (OM)

(73) Assignee: Sultan Qaboos University, Al-Khodh (OM)

( * ) Notice: Subject to any disclaimer, the term of this patent is extended or adjusted under 35 U.S.C. 154(b) by 0 days.

(21) Appl. No.: 15/686,675

(22) Filed: Aug. 25, 2017

(65) Prior Publication Data

US 2018/0105582 A1    Apr. 19, 2018

(30) Foreign Application Priority Data

Oct. 14, 2016    (ZA) ........................ 16/7084

(51) Int. Cl.
| | |
|---|---|
| C07K 16/10 | (2006.01) |
| A23L 33/105 | (2016.01) |
| A61K 35/20 | (2006.01) |
| A61K 36/285 | (2006.01) |
| C07K 16/04 | (2006.01) |
| A61K 36/28 | (2006.01) |
| A23C 9/20 | (2006.01) |
| A23C 9/00 | (2006.01) |
| A61K 39/00 | (2006.01) |

(52) U.S. Cl.
CPC ............ C07K 16/1045 (2013.01); A23C 9/20 (2013.01); A23L 33/105 (2016.08); A61K 35/20 (2013.01); A61K 36/28 (2013.01); A61K 36/285 (2013.01); C07K 16/04 (2013.01); A23C 9/00 (2013.01); A61K 2039/53 (2013.01); C07K 2317/12 (2013.01); C07K 2317/22 (2013.01); C07K 2317/569 (2013.01); C07K 2317/76 (2013.01)

(58) Field of Classification Search
None
See application file for complete search history.

(56) References Cited

U.S. PATENT DOCUMENTS

| | | | |
|---|---|---|---|
| 2005/0129780 A1 | 6/2005 | Holcomb-Halstead | |
| 2011/0104163 A1 | 5/2011 | Dimitrov | |
| 2013/0028968 A1* | 1/2013 | Huang .................. | A61K 36/06 424/451 |
| 2013/0095150 A1 | 4/2013 | Elaraqi | |
| 2014/0037722 A1* | 2/2014 | Mousa .................. | A61K 9/4866 424/452 |

FOREIGN PATENT DOCUMENTS

| | | | |
|---|---|---|---|
| CN | 105412405 | * | 3/2016 |
| WO | 2010072327 A2 | | 7/2010 |
| WO | 2011039574 A1 | | 4/2011 |
| WO | WO 2011039574 | * | 4/2011 |
| WO | 2012027440 A1 | | 3/2012 |

OTHER PUBLICATIONS

Sequence alignment of instant Seq Id No. 3 with GenEmbl database access No. AY271690 by Tebit et al. in Virology. 2003; 313 (2) 2: 645-652.*
Chhatbar et al. (Drug Discovery Today. Nov. 2011; 16 (21/22): 948-956).*
Parast et al. (Journal of the American Statistical Association. 2014; 109 (505): 384-394).*
Pitcher et al. (Nature Medicine. 1999; 5 (5): 518-525).*
Courtney et al. (PLoS One. Mar. 2017; https://doi.org/10.1371/journal.pone. 01737015).*
Wakayo et al. (African Journal of Pharmacy and Pharmacology. Sep. 2016; 10 (36): 778-784).*
Scheid et al. (Science. Sep. 2011; 333: 16330-1637).*
Excler et al. (Vaccine. 2015; 33: D4-D12).*
V. Cortez-Retamozo, "Efficient Tumor Targeting by Single Domain Antibody Fragments of Camels", International Journal Cancer (98) pp. 456-462 (2002).
S.S. Hasson, "The Past, Current and Future Trends in DNA Vaccine Immunisations", Asian Pacific Journal of Tropical Biomedicine, (5)5 pp. 344-353 (2015).
Guido Vanham "Can Immunotherapy Be Useful as a 'Functional Cure' for Infection with Human Immunodeficiency Virus-1", Retrovirology (9)72 pp. 1-21 (2012).
Clarisse Lorin, "A Single injection of Recombinant Measles Virus Vaccines Expressing Human Immunodeficiency Virus (HIV) Type 1 Clade B Envelope Glycoproteins Induces Neutralizing Antibodies and Cellular Immune Responses to HIV", Journal of Virology, (78)1 pp. 146-157 92004).
Sidgi S. A. A. Hasson, "In Vitro Apoptosis Triggering in the BT-474 Human Breast Cancer Cell Line by Lyophilised Camel's Milk", Asian Pacific Journal of Cancer Prevention, (16)15 pp. 6651-6661 (2015).

* cited by examiner

Primary Examiner — Shanon A. Foley
(74) Attorney, Agent, or Firm — Richard C. Litman

(57) ABSTRACT

A therapeutic composition of camel milk can include an herbal composition having solid material or liquid extracts from the solid material of at least one of *Saussurea acrophila* Diels, *Saussurea ceratocarpa*, and *Aucklandia lappa* Decne. The solid material may include one or more of parts or the whole of the stem, the bark, the flowers and the roots of one or more, but preferably all of *Saussurea acrophila* Diels, *Saussurea ceratocarpa*, and *Aucklandia lappa* Decne. The therapeutic composition can include camel milk, alone, or in combination with the herbal composition. The camel milk can be HIV-immunized camel milk. The HIV-immunized camel milk can be obtained by immunizing a camel against HIV by administering to the camel the modified DNA plasmids of SEQ. ID No.: 3 and SEQ ID No.: 4 and obtaining the milk from the immunized camel.

6 Claims, 3 Drawing Sheets

Specification includes a Sequence Listing.

```
                        SEQUENCE LISTING

<160> NUMBER OF SEQ ID NOS: 4

<210> SEQ ID NO 1
<211> LENGTH: 12256
<212> TYPE: DNA
<213> ORGANISM: Artificial Sequence
<220> FEATURE:
<223> OTHER INFORMATION: Plasmid

<400> SEQUENCE: 1
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga cccttttagt cagtgtggaa aatctctagc     180
agtggcgccc gaacagggac atgaaagcga agggaaacc agaggagctc tctcgacgca      240
ggactcggct tgctgaagcg cgcacggcaa gaggcgaggg gcggcgactg gtgagtacgc     300
caaaaatttt gactagcgga ggctagaagg agagagatgg gtgcgagagc gtcagtatta     360
agcgggggaa aattagatcg atgggaaaaa attcggttaa ggccaggggg aaagaaaaaa     420
tataaattaa aacatatagt atgggcaagc agggagctag aacgattcgc agttaatcct     480
ggcctgttag aaacatcaga aggctgtaga caaatactgg gacagctaca accatccctt     540
```

```
cagacaggat cagaagaacg tagatcatta tataatacag tagcaaccct ctattgtgtg    600
catcaaagga tagagataaa agacaccaag gaagctttag acaagataga ggaagagcaa    660
aacaaaagta agaaaaaagc acagcaagca gcagctgaca caggacacag cagccaggtc    720
agccaaaatt accctatagt gcagaacatc caggggcaaa tggtacatca ggccatatca    780
cctagaactt taaatgcatg ggtaaaagta gtagaagaga aggctttcag cccagaagtg    840
atacccatgt tttcagcatt atcagaagga gccaccccac aagatttaaa caccatgcta    900
aacacagtgg ggggacatca agcagccatg caaatgttaa aagagaccat caatgaggaa    960
gctgcagaat gggatagagt gcatccagtg catgcagggc ctattgcacc aggccagatg   1020
agagaaccaa ggggaagtga catagcagga actactagta cccttcagga acaaatagga   1080
tggatgacac ataatccacc tatcccagta ggagaaatct ataaaagatg gataatcctg   1140
ggattaaata aaatagtaag aatgtatagc cctaccagca ttctggacat aagacaagga   1200
ccaaaggaac cctttagaga ctatgtagac cgattctata aaactctaag agccgagcaa   1260
gcttcacaag aggtaaaaaa ttggatgaca gaaaccttgt tggtccaaaa tgcgaaccca   1320
gattgtaaga ctattttaaa agcattggga ccaggagcga cactagaaga atgatgaca   1380 gcatgtcagg gagtgggggg acccggccat aaagcaagag ttttggctga agcaatgagc   1440
caagtaacaa atccagctac cataatgata cagaaaggca attttaggaa ccaaagaaag   1500
actgttaagt gtttcaattg tggcaaagaa gggcacatag ccaaaaattg cagggcccct   1560
aggaaaaagg gctgttggaa atgtggaaag gaaggacacc aaatgaaaga ttgtactgag   1620
agacaggcta ttttttagg gaagatctgg ccttcccaca agggaaggcc agggaattt    1680 cttcagagca gaccagagcc aacagcccca ccagaagaga gcttcaggtt tggggaagag   1740
acaacaactc cctctcagaa gcaggagccg atagacaagg aactgtatcc tttagcttcc   1800
ctcagatcac tctttggcag cgaccctcg tcacaataaa gatagggggg caattaaagg   1860
aagctctatt agatacagga gcagatgata cagtattaga agaaatgaat ttgccaggaa   1920
gatggaaacc aaaaatgata gggggaattg gaggttttat caaagtaaga cagtatgatc   1980
agatactcat agaaatctgc ggacataaag ctataggtac agtattagta ggacctacac   2040
ctgtcaacat aattggaaga aatctgttga ctcagattgg ctgcacttta aattttccca   2100
ttagtcctat tgagactgta ccagtaaaat taaagccagg aatggatggc ccaaaagtta   2160
aacaatggcc attgacagaa gaaaaaataa aagcattagt agaaatttgt acagaaatgg   2220
aaaaggaagg aaaaatttca aaaattgggc ctgaaaatcc atacaatact ccagtatttg   2280
ccataaagaa aaaagacagt actaaatgga gaaaattagt agatttcaga gaacttaata   2340
agagaactca agatttctgg gaagttcaat taggaatacc acatcctgca gggttaaaac   2400
agaaaaaatc agtaacagta ctggatgtgg gcgatgcata tttttcagtt cccttagata   2460
aagacttcag gaagtatact gcatttacca tacctagtat aaacaatgag acaccaggga   2520
ttagatatca gtacaatgtg cttccacagg gatggaaagg atcaccagca atattccagt   2580
gtagcatgac aaaaatctta gagcctttta gaaaacaaaa tccagacata gtcatctatc   2640
aatacatgga tgatttgtat gtaggatctg acttagaaat agggcagcat agaacaaaaa   2700
tagaggaact gagacaacat ctgttgaggt ggggatttac cacaccagac aaaaacatc   2760 agaaagaacc tccattcctt tggatgggtt atgaactcca tcctgataaa tggacagtac   2820
agcctatagt gctgccagaa aaggacagct ggactgtcaa tgacatacag aaattagtgg   2880
gaaaattgaa ttgggcaagt cagatttatg cagggattaa agtaaggcaa ttatgtaaac   2940
```

```
ttcttagggg aaccaaagca ctaacagaag tagtaccact aacagaagaa gcagagctag      3000
aactggcaga aaacagggag attctaaaag aaccggtaca tggagtgtat tatgacccat      3060
caaaagactt aatagcagaa atacagaagc aggggcaagg ccaatggaca tatcaaattt      3120
atcaagagcc atttaaaaat ctgaaaacag gaaagtatgc aagaatgaag ggtgcccaca      3180
ctaatgatgt gaaacaatta acagaggcag tacaaaaaat agccacagaa agcatagtaa      3240
tatggggaaa gactcctaaa tttaaattac ccatacaaaa ggaaacatgg gaagcatggt      3300
ggacagagta ttggcaagcc acctggattc ctgagtggga gtttgtcaat acccctccct      3360
tagtgaagtt atggtaccag ttagagaaag aacccataat aggagcagaa actttctatg      3420
tagatggggc agccaatagg gaaactaaat taggaaaagc aggatatgta actgacagag      3480
gaagacaaaa agttgtcccc ctaacggaca acaaaatca gaagactgag ttacaagcaa       3540
ttcatctagc tttgcaggat tcgggattag aagtaaacat agtgacagac tcacaatatg      3600
cattgggaat cattcaagca caaccagata agagtgaatc agagttagtc agtcaaataa      3660
tagagcagtt aataaaaaag gaaaaagtct acctggcatg ggtaccagca cacaaaggaa      3720
ttggaggaaa tgaacaagta gataaattgg tcagtgctgg aatcaggaaa gtactatttt      3780
tagatggaat agataaggcc caagaagaac atgagaaata tcacagtaat ggagagcaa       3840 tggctagtga ttttaaccta ccacctgtag tagcaaaaga aatagtagcc agctgtgata      3900
aatgtcagct aaaaggggaa gccatgcatg gacaagtaga ctgtagccca ggaatatggc      3960
agctagattg tacacattta gaaggaaaag ttatcttggt agcagttcat gtagccagtg      4020
gatatataga agcagaagta attccagcag agacagggca agaaacagca tacttcctct      4080
taaaattagc aggaagatgg ccagtaaaaa cagtacatac agacaatggc agcaatttca      4140
ccagtactac agttaaggcc gcctgttggt gggcgggat caagcaggaa tttggcattc      4200
cctacaatcc ccaaagtcaa ggagtaatag aatctatgaa taaagaatta agaaaaatta      4260
taggacaggt aagagatcag gctgaacatc ttaagacagc agtacaaatg gcagtattca      4320
tccacaattt taaaagaaaa ggggggattg ggggtacag tgcagggaa agaatagtag        4380 acataatagc aacagacata caaactaaag aattacaaaa acaaattaca aaaattcaaa      4440
attttcgggt ttattacagg gacagcagag atccagtttg gaaaggacca gcaaagctcc      4500
tctggaaagg tgaaggggca gtagtaatac aagataatag tgcataaaa gtagtgccaa       4560 gaagaaaagc aaagatcatc agggattatg gaaacagat ggcaggtgat gattgtgtgg       4620
caagtagaca ggatgaggat taacacatgg aaaagattag taaaacacca tatgtatatt      4680
tcaaggaaag ctaaggactg gttttataga catcactatg aaagtactaa tccaaaaata      4740
agttcagaag tacacatccc actagggat gctaaattag taataacaac atattggggt       4800
ctgcatacag gagaaagaga ctggcatttg ggtcagggag tctccataga atggaggaaa      4860
aagagatata gcacacaagt agaccctgac ctagcagacc aactaattca tctgcactat      4920
tttgattgtt tttcagaatc tgctataaga aataccatat taggacgtat agttagtcct      4980
aggtgtgaat atcaagcagg acataacaag gtaggatctc tacagtactt ggcactagca      5040
gcattaataa aaccaaaaca gataaagcca cctttgccta gtgttaggaa actgacagag      5100
gacagatgga acaagcccca gaagaccaag ggccacagag ggagccatac aatgaatgga      5160
cactagagct tttagaggaa cttaagagtg aagctgttag acatttcct aggatatggc       5220 tccataactt aggacaacat atctatgaaa cttacgggga tacttgggca ggagtggaag      5280
```

-continued

```
ccataataag aattctgcaa caactgctgt ttatccattt cagaattggg tgtcgacata    5340
gcagaatagg cgttactcga cagaggagag caagaaatgg agccagtaga tcctagacta    5400
gagccctgga agcatccagg aagtcagcct aagactgctt gtaccacttg ctattgtaaa    5460
aagtgttgct ttcattgcca agtttgcttc ataacaaaag cttaggcat  ctcctatggc    5520
aggaagaagc ggagacagcg acgaagagct cctcaagaca gtgagactca tcaagtttct    5580
ctatcaaagc agtaagtagt acatgtaatg caagctttac aaatatcagc aatagtagga    5640
ttagtagtag cagcaataat agcaatagtt gtgtggacca tagtattcat agaatatagg    5700
aaaatattaa ggcaaagaaa aatagacagg ataattgata gaataataga aagagcagaa    5760
gacagtggca atgagagtga cggagatcag gaagagttat cagcactggt ggagatgggg    5820
catcatgctc cttgggatgt taatgatctg taatgctgag gaaaaattgt gggtcacagt    5880
ctattatggg gtacctgtgt ggaaagaagc aaccaccact ctattttgtg catcagatgc    5940
taaagcatat gatacagagg tacataatgt ttgggccaca catgcctgtg tacccacaga    6000
ccccaaccca caagaagtag aattggaaaa tgtgacagaa aattttaaca tgtggaaaaa    6060
taacatggta gaacagatgc atgaggatat aatcagttta tgggatcaaa gcctaaagcc    6120
atgtgtaaaa ttaactccac tctgtgttac tttaaattgc actgatttga ggaatgctac    6180
taatgggaat gacactaata ccactagtag tagcagggaa atgatggggg gaggagaaat    6240
gaaaaattgc tctttcaaaa tcaccacaaa cataagaggt aaggtgcaga agaatatgc     6300
acttttttat gaacttgata tagtaccaat agataataat agtaataata gatataggtt    6360
gataagttgt aacaccctcag tcattacaca ggcctgtcca agatatcct  ttgagccaat    6420
tcccatacat tattgtgccc cggctggttt tgcgattcta aagtgtaaag ataagaagtt    6480
caatggaaaa ggaccatgtt caaatggcag cacagtacaa tgtacacatg gattaggcc     6540
agtagtatca actcaactgc tgttaaatgg cagtctagca gaagaagagg tagtaattag    6600
atccgaaaat ttcgcggaca atgctaaaac cataatagta cagctgaatg aatctgtaga    6660
aattaattgt acaagaccca caacaatac aagaaaaagt atacatatag gaccaggcag     6720
agcattatat acaacaggag aaataatagg agatataaga caagcacatt gtaaccttag    6780
tagagcaaag tggaatgaca ctttaaataa gatagttata aaattaagag aacaatttgg    6840
gaataaaaca atagtcttta agcattcctc aggaggggac ccagaaattg tgacgcacag    6900
ttttaattgt ggaggggaat ttttctactg taattcaaca caactgttta atagtacttg    6960
gaatgttact gaagagtcaa ataacactgt agaaaataac acaatcacac tcccatgcag    7020
aataaaacaa attataaaca tgtggcagaa agtaggaaga gcaatgtatg ccccctcccat    7080
cagaggacaa attagatgtt catcaaatat tacagggctg ctattaacaa gagatggtgg    7140
tccagaggac aacaagaccg aggtcttcag acctggagga ggagatatga gggacaattg    7200
gagaagtgaa ttatataaat ataaagtagt aaaaattgaa ccattaggag tagcacccac    7260
caaggcaaag agaagagtgg tgcagagaga aaaaagagca gtgggaatag agctgtgtt     7320
ccttgggttc ttgggagcag caggaagcac tatgggcgca gcgtcaatga cgctgacggt    7380
acaggccaga ctattattgt ctggtatagt gcaacagcag aacaatctgc tgagggctat    7440
tgaggcgcaa cagcatctgt tgcaactcac agtctgggc  atcaagcagc tccaggcaag    7500
agtcctggct gtggaaagat acctaaggga tcaacagctc ctgggaattt ggggttgctc    7560
tggaaaactc atttgcacca ctgctgtgcc ttggaatgct agttggagta ataaatctct    7620
gaataagatt tgggataaca tgacctggat ggagtgggac agagaaatta caattacac     7680
```

```
aagcataata tatagcttaa ttgaagaatc gcagaaccaa caagaaaaga atgaacaaga    7740
attattagaa ttagacaaat gggcaagttt gtggaattgg tttgacataa cagaatggct    7800
gtggtatata aaatattca taatgataat aggaggcttg ataggtttaa gaatagtttt    7860
ttctgtactt tctataatga atagagttag gcagggatac tcaccattat cgtttcagac    7920
ccacctccca gcctcgaggg gacccgacag gcccggagga atcgaagaag aaggtggaga    7980
gagagacaga gacagatccg gtcgattagt gaacggatcc ttagcactta tctgggacga    8040
tctgcggagc ctgtgcctct tcagctacca ccgcttgaga gacttactct tgattgtaac    8100
gaggattgtg gaacttctgg gacgcagggg gtgggaagcc ctcaaatatt ggtggaatct    8160
cctacaatat tggagtcagg agctaaagaa tagtgctgtt agcttgctca atgccacagc    8220
tatagcagta gctgagggga cagatagggt tatagaagta gtacaagaag cttatagagc    8280
tattcgccac atacctagaa gaataagaca gggcttggaa aggattttgc tataagatgg    8340
gtggcaagtg gtcaaaaagt agtgtggttg atggcctgc tgtaagggaa agaatgagac    8400
gagctgagcc agcagcagat ggggtgggag cagcatctcg agacctagaa aaacatggag    8460
caatcacaag tagcaacaca gcagctaaca atgctgcttg tgcctggcta aagcacaag    8520 aggaggagaa ggtgggtttt ccagtcacac ctcaggtacc tttaagacca atgacttaca    8580
aggcagctgt agatcttagc cactttttaa aagaaaaggg gggactggaa gggctaattc    8640
actcccaacg aagacaagat atccttgatc tgtggatcta ccacacacaa ggctacttcc    8700
ctgattggca gaactacaca ccaggaccag ggatcagata tccactgacc tttggatggc    8760
gctacaagct agtaccagtt gagccagaga agttagaaga agccaacaaa ggagagaaca    8820
ccagcttgtt acaccctgtg agcctgcatg gaatggatga cccggagaga gaagtgttag    8880
agtggaggtt tgacagccgc ctagcatttc atcacgtggc ccgagagctg catccggagt    8940
acttcaagaa ctgctgatat cgagcttgct acaagggact ttccgctggg gactttccag    9000
ggaggcgtgg cctgggcggg actggggagt ggcgagccct cagatcctgc atataagcag    9060 ctgcttttg cctgtactgg gtctctctgg ttagaccaga tctgagcctg ggagctctct    9120
ggctaactag ggaacccact gcttaagcct caataaagct tgccttgagt gcttcaagta    9180
gtgtgtgccc gtctgttgtg tgactctggt aactagagat ccctcagacc cttttagtca    9240
gtgtggaaaa tctctagcag tcacgtaact ctgaaaaggt caaagatatt gatgcttgat    9300
acagaaggaa gggaatacca gtgagttgtc tggactacac taaacatacc tgaaatctga    9360
gttcgagaag tataatagaa ctggactcca aattaagtct cagttgcaaa ctggattaat    9420
gggggataga tttctatcta gagggggca ggtgaccttc agaccttggc actggaggtg    9480
gcccggcaga agcgcggcat cgtggatcag tgctgcacca gcatctgctc tctctaccaa    9540
ctggagaact actgcaacta ggcccaccac tacccctgtcc accctctgc aatgaataaa    9600 acctttgaaa gagcactaca agttgtgtgt acatgcgtgc atgtgcatat gtggtgcggg    9660
gggaacatga gtggggctgg ctggagtggc gatgataagc tgtcaaacat gagaattctt    9720
gaagacgaaa gggcctcgtg atacgcctat ttttataggt taatgtcatg ataataatgg    9780
tttcttagac gtcaggtggc acttttcggg gaaatgtgcg cggaacccct atttgtttat    9840
ttttctaaat acattcaaat atgtatccgc tcatgagaca ataaccctga taaatgcttc    9900
aataatattg aaaaggaag agtatgagta ttcaacattt ccgtgtcgcc cttattccct    9960
tttttgcggc attttgcctt cctgtttttg ctcacccaga aacgctggtg aaagtaaaag    10020
```

```
atgctgaaga tcagttgggt gcacgagtgg gttacatcga actggatctc aacagcggta    10080
agatccttga gagttttcgc cccgaagaac gttttccaat gatgagcact tttaaagttc    10140
tgctatgtgg cgcggtatta tcccgtgttg acgccgggca agagcaactc ggtcgccgca    10200
tacactattc tcagaatgac ttggttgagt actcaccagt cacagaaaag catcttacgg    10260
atggcatgac agtaagagaa ttatgcagtg ctgccataac catgagtgat aacactgcgg    10320
ccaacttact tctgacaacg atcggaggac cgaaggagct aaccgctttt ttgcacaaca    10380
tgggggatca tgtaactcgc cttgatcgtt gggaaccgga gctgaatgaa gccataccaa    10440
acgacgagcg tgacaccacg atgcctgcag caatggcaac aacgttgcgc aaactattaa    10500
ctggcgaact acttactcta gcttcccggc aacaattaat agactggatg gaggcggata    10560
aagttgcagg accacttctg cgctcggccc ttccggctgg ctggtttatt gctgataaat    10620
ctggagccgg tgagcgtggg tctcgcggta tcattgcagc actggggcca gatggtaagc    10680
cctcccgtat cgtagttatc tacacgacgg ggagtcaggc aactatggat gaacgaaata    10740
gacagatcgc tgagataggt gcctcactga ttaagcattg gtaactgtca gaccaagttt    10800
actcatatat actttagatt gatttaaaac ttcatttta atttaaaagg atctaggctg    10860
ctgcttgcaa acaaaaaaac caccgctacc agcggtggtt tgtttgccgg atcaagagct    10920
accaactctt tttccgaagg taactggctt cagcagagcg cagataccaa atactgtcct    10980
tctagtgtag ccgtagttag gccaccactt caagaactct gtagcaccgc ctacatacct    11040
cgctctgcta atcctgttac cagtggctgc tgccagtggc gataagtcgt gtcttaccgg    11100
gttggactca agacgatagt taccggataa ggcgcagcgg tcgggctgaa cggggggttc    11160
gtgcacacag cccagcttgg agcgaacgac ctacaccgaa ctgagatacc tacagcgtga    11220
gctatgagaa agcgccacgc ttcccgaagg agaaaggcg acaggtatc cggtaagcgg    11280 cagggtcgga acaggagagc gcacgaggga gcttccaggg ggaaacgcct ggtatcttta    11340
tagtcctgtc gggtttcgcc acctctgact tgagcgtcga ttttgtgat gctcgtcagg    11400 ggggcggagc ctatggaaaa acgccagcaa cggagatgcg ccgcgtgcgg ctgctggaga    11460
tggcggacgc gatggatatg ttctgccaag ggttggtttg cgcattcaca gttctccgca    11520
agaattgatt ggctccaatt cttggagtgg tgaatccgtt agcgaggtgc cgccggcttc    11580
cattcaggtc gaggtggccc ggctccatgc accgcgacgc aacgcgggga ggcagacaag    11640
gtatagggcg gcgcctacaa tccatgccaa cccgttccat gtgctcgccg aggcggcata    11700
aatcgccgtg acgatcagcg gtccaatgat cgaagttagg ctggtaagag ccgcgagcga    11760
tccttgaagc tgtccctgat ggtcgtcatc tacctgcctg gacagcatgg cctgcaacgc    11820
gggcatcccg atgccgccgg aagcgagaag aatcataatg gggaaggcca tccagcctcg    11880
cgtcggggag cttttttgcaa aagcctaggc ctccaaaaa gcctcctcac tacttctgga    11940
atagctcaga ggccgaggcg gcctcggcct ctgcataaat aaaaaaaatt agtcagccat    12000
ggggcggaga atgggcggaa ctgggcggag ttaggggcgg gatgggcgga gttaggggcg    12060
ggactatggt tgctgactaa ttgagatgca tgttcgaatc gcgaccgcgg tccggagtac    12120
ttcaagaact gctgatatcg agcttgctac aagggactt ccgctgggga ctttccaggg    12180
aggcgtggcc tgggcgggac tggggagtgg cgagccctca gatcctgcat ataagcagct    12240 gcttttttgcc tgtact                                                  12256
```

<210> SEQ ID NO 2
<211> LENGTH: 14825

```
<212> TYPE: DNA
<213> ORGANISM: Artificial Sequence
<220> FEATURE:
<223> OTHER INFORMATION: Plasmid

<400> SEQUENCE: 2
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
atgaaggaga gaacaacagc ttgttacacc ctatgagcca gcatgggatg gaggacccgg     240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccaggggag gtgtggcctg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata agcttgcct      540
tgagtgctca agtagtgtg tgcccgtctg ttgtgtgact ctggtaacta gagatccctc     600
agacccttt agtcagtgtg gaaaatctct agcagtggcg cccgaacagg gacttgaaag     660
cgaaagtaaa gccagaggag atctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcggta ttaagcgggg gagaattaga taaatgggaa     840
aaaattcggt taaggccagg gggaagaaa caatataaac taaaacatat agtatgggca     900
agcagggagc tagaacgatt cgcagttaat cctggccttt tagagacatc agaaggctgt     960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200
ctccaggggc aaatggtaca tcaggccata tcacctagaa ctttaaatgc atgggtaaaa    1260
gtagtagaag agaaggcttt cagcccagaa gtaatacccc tgttttcagc attatcagaa    1320
ggagccaccc cacaagattt aaataccatg ctaaacacag tggggggaca tcaagcagcc    1380
atgcaaatgt taaaagagac catcaatgag gaagctgcag aatgggatag attgcatcca    1440
gtgcatgcag ggcctattgc accaggccag atgagagaac caaggggaag tgacatagca    1500
ggaactacta gtacccttca ggaacaaata ggatggatga cacataatcc acctatccca    1560
gtaggagaaa tctataaaag atggataatc ctgggattaa ataaaatagt aagaatgtat    1620
agccctacca gcattctgga cataagacaa ggaccaaagg aacccttag agactatgta    1680
gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga gaaatgatg acagcatgtc agggagtggg gggacccggc    1860
cataaagcaa gagttttggc tgaagcaatg agccaagtaa caaatccagc taccataatg    1920
atacagaaag gcaattttag gaaccaaaga aagactgtta agtgtttcaa ttgtggcaaa    1980
gaagggcaca tagccaaaaa ttgcagggcc cctaggaaaa agggctgttg gaaatgtgga    2040
aaggaaggac accaaatgaa agattgtact gagagacagg ctaatttttt agggaagatc    2100
tggccttccc acaagggaag gccagggaat tttcttcaga gcagaccaga gccaacagcc    2160
```

```
ccaccagaag agagcttcag gtttggggaa gagacaacaa ctccctctca gaagcaggag    2220
ccgatagaca aggaactgta tcctttagct tccctcagat cactctttgg cagcgacccc    2280
tcgtcacaat aaagataggg gggcaattaa aggaagctct attagataca ggagcagatg    2340
atacagtatt agaagaaatg aatttgccag gaagatggaa accaaaaatg ataggggaa     2400
ttggaggttt tatcaaagta agacagtatg atcagatact catagaaatc tgcggacata    2460
aagctatagg tacagtatta gtaggaccta cacctgtcaa cataattgga agaaatctgt    2520
tgactcagat tggctgcact ttaaattttc ccattagtcc tattgagact gtaccagtaa    2580
aattaaagcc aggaatggat ggcccaaaag ttaaacaatg gccattgaca gaagaaaaaa    2640
taaaagcatt agtagaaatt tgtacagaaa tggaaaagga aggaaaaatt tcaaaaattg    2700
ggcctgaaaa tccatacaat actccagtat ttgccataaa gaaaaagac agtactaaat     2760
ggagaaaatt agtagatttc agagaactta ataagagaac tcaagatttc tgggaagttc    2820
aattaggaat accacatcct gcagggttaa aacagaaaaa atcagtaaca gtactggatg    2880
tgggcgatgc atatttttca gttcccttag ataaagactt caggaagtat actgcattta    2940
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
ctgacttaga aatagggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540
agcaggggca aggccaatgg acatatcaaa tttatcaaga gccatttaaa aatctgaaaa    3600
caggaaagta tgcaagaatg aagggtgccc acactaatga tgtgaaacaa ttaacagagg    3660
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaacttttct atgtagatgg ggcagccaat agggaaacta    3900
aattaggaaa agcaggatat gtaactgaca gaggaagaca aaaagttgtc cccctaacgg    3960
acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagataaat    4200
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
```

```
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaaagaaaa ttataggaca ggtaagagat caggctgaac    4740
atcttaagac agcagtacaa atggcagtat tcatccacaa ttttaaaaga aaaggggga     4800 ttgggggggta cagtgcaggg gaaagaatag tagacataat agcaacagac atacaaacta   4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gttttttcaga atctgctata    5400 agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggacactaga gcttttagag gaacttaaga    5640
gtgaagctgt tagacatttt cctaggatat ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcagaat aggcgttact cgacagagga    5820
gagcaagaaa tggagccagt agatcctaga ctagagccct ggaagcatcc aggaagtcag    5880
cctaaaactg cttgtaccaa ttgctattgt aaaaagtgtt gctttcattg ccaagtttgt    5940
ttcatgacaa aagccttagg catctcctat ggcaggaaga agcggagaca gcgacgaaga    6000
gctcatcaga acagtcagac tcatcaagct tctctatcaa agcagtaagt agtacatgta    6060
atgcaaccta atatagtagc aatagtagca ttagtagtag caataataat agcaatagtt    6120
gtgtggtcca tagtaatcat agaatatagg aaaatattaa gacaagaaa aatagacagg     6180 ttaattgata gactaataga aagagcagaa gacagtggca atgagagtga aggagaagta    6240
tcagcacttg tggagatggg ggtggaaatg gggcaccatg ctccttggga tattgatgat    6300
ctgtagtgct acagaaaaat tgtgggtcac agtctattat ggggtacctg tgtggaagga    6360
agcaaccacc actctatttt gtgcatcaga tgctaaagca tatgatacag aggtacataa    6420
tgtttgggcc acacatgcct gtgtacccac agaccccaac ccacaagaag tagtattggt    6480
aaatgtgaca gaaaatttta acatgtggaa aaatgacatg gtagaacaga tgcatgagga    6540
tataatcagt ttatgggatc aaagcctaaa gccatgtgta aaattaaccc cactctgtgt    6600
tagtttaaag tgcactgatt tgaagaatga tactaatacc aatagtagta gcgggagaat    6660
gataatggag aaaggagaga taaaaaactg ctctttcaat atcagcacaa gcataagaga    6720
taaggtgcag aaagaatatg cattctttta taaacttgat atagtaccaa tagataatac    6780
cagctatagg ttgataagtt gtaacacctc agtcattaca caggcctgtc caaaggtatc    6840
ctttgagcca attcccatac attattgtgc cccggctggt tttgcgattc taaaatgtaa    6900
```

```
taataagacg ttcaatggaa caggaccatg tacaaatgtc agcacagtac aatgtacaca    6960
tggaatcagg ccagtagtat caactcaact gctgttaaat ggcagtctag cagaagaaga    7020
tgtagtaatt agatctgcca atttcacaga caatgctaaa accataatag tacagctgaa    7080
cacatctgta gaattaatt gtacaagacc caacaacaat acaagaaaaa gtatccgtat     7140
ccagagggga ccagggagag catttgttac aataggaaaa ataggaaata tgagacaagc    7200
acattgtaac attagtagag caaaatggaa tgccacttta aaacagatag ctagcaaatt    7260
aagagaacaa tttggaaata taaaacaat aatctttaag caatcctcag gaggggaccc     7320
agaaattgta acgcacagtt ttaattgtgg aggggaattt ttctactgta attcaacaca    7380 actgttaat agtacttggt ttaatagtac ttggagtact gaagggtcaa ataacactga     7440
aggaagtgac acaatcacac tcccatgcag aataaaacaa tttataaaca tgtggcagga    7500
agtaggaaaa gcaatgtatg cccctcccat cagtggacaa attagatgtt catcaaatat    7560
tactgggctg ctattaacaa gagatggtgg taataacaac aatgggtccg agatcttcag    7620
acctggagga ggcgatatga gggacaattg gagaagtgaa ttatataaat ataaagtagt    7680
aaaaattgaa ccattaggag tagcaccccac caaggcaaag agaagagtgg tgcagagaga    7740
aaaaagagca gtgggaatag gagctttgtt ccttgggttc ttgggagcag caggaagcac    7800
tatgggcgca gcgtcaatga cgctgacggt acaggccaga caattattgt ctgatatagt    7860
gcagcagcag aacaatttgc tgagggctat tgaggcgcaa cagcatctgt tgcaactcac    7920
agtctggggc atcaaacagc tccaggcaag aatcctggct gtggaaagat acctaaagga    7980
tcaacagctc ctggggattt ggggttgctc tggaaaactc atttgcacca ctgctgtgcc    8040
ttggaatgct agttggagta ataaatctct ggaacagatt tggaataaca tgacctggat    8100
ggagtgggac agagaaatta acaattacac aagcttaata cactccttaa ttgaagaatc    8160
gcaaaaccag caagaaaaga atgaacaaga attattggaa ttagataaat gggcaagttt    8220
gtggaattgg tttaacataa caaattggct gtggtatata aaattattca taatgatagt    8280
aggaggcttg gtaggtttaa gaatagtttt tgctgtactt tctatagtga atagagttag    8340
gcagggatat tcaccattat cgtttcagac ccacctccca atcccgaggg gacccgacag    8400
gcccgaagga atagaagaag aaggtggaga gagagacaga gacagatcca ttcgattagt    8460
gaacggatcc ttagcactta tctgggacga tctgcggagc ctgtgcctct tcagctacca    8520
ccgcttgaga gacttactct tgattgtaac gaggattgtg gaacttctgg gacgcagggg    8580
gtgggaagcc ctcaaatatt ggtggaatct cctacagtat tggagtcagg aactaaagaa    8640
tagtgctgtt aacttgctca atgccacagc catagcagta gctgagggga cagatagggt    8700
tatagaagta ttacaagcag cttatagagc tattcgccac atacctagaa gaataagaca    8760
gggcttggaa aggattttgc tataagatgg gtggcaagtg gtcaaaaagt agtgtgattg    8820
gatggcctgc tgtaagggaa agaatgagac gagctgagcc agcagcagat ggggtgggag    8880
cagtatctcg agacctagaa aaacatggag caatcacaag tagcaataca gcagctaaca    8940
atgctgcttg tgcctggcta gaagcacaag aggaggaaga ggtgggtttt ccagtcacac    9000
ctcaggtacc tttaagacca atgacttaca aggcagctgt agatcttagc cacttttaa    9060 aagaaaaggg gggactggaa gggctaattc actcccaaag aagacaagat atccttgatc    9120
tgtggatcta ccacacacaa ggctacttcc ctgattggca gaactacaca ccagggccag    9180
gggtcagata tccactgacc tttggatggt gctacaagct agtaccagtt gagccagata    9240
aggtagaaga ggccaataaa ggagagaaca ccagcttgtt acaccctgtg agcctgcatg    9300
```

```
gaatggatga ccctgagaga gaagtgttag agtggaggtt tgacagccgc ctagcatttc   9360
atcacgtggc ccgagagctg catccggagt acttcaagaa ctgctgacat cgagcttgct   9420
acaagggact ttccgctggg actttccag  ggaggcgtgg cctgggcggg actggggagt   9480
ggcgagccct cagatgctgc atataagcag ctgcttttg  cctgtactgg gtctctctgg   9540
ttagaccaga tctgagcctg ggagctctct ggctaactag ggaacccact gcttaagcct   9600
caataaagct tgccttgagt gcttcaagta gtgtgtgccc gtctgttgtg tgactctggt   9660
aactagagat ccctcagacc cttttagtca gtgtggaaaa tctctagcac ccaggaggta   9720
gaggttgcag tgagccaaga tcgcgccact gcattccagc ctgggcaaga aaacaagact   9780
gtctaaaata ataataataa gttaagggta ttaaatatat ttatacatgg aggtcataaa   9840
aatatatata tttgggctgg gcgcagtggc tcacacctgc gcccggccct ttgggaggcc   9900
gaggcaggtg gatcacctga gtttgggagt ccagaccag  cctgaccaac atggagaaac   9960
cccttctctg tgtattttta gtagatttta ttttatgtgt attttattca caggtatttc  10020
tggaaaactg aaactgtttt tcctctactc tgataccaca agaatcatca gcacagagga  10080
agacttctgt gatcaaatgt ggtgggagag ggaggttttc accagcacat gagcagtcag  10140
ttctgccgca gactcggcgg gtgtccttcg gttcagttcc aacaccgcct gcctggagag  10200
aggtcagacc acagggtgag ggctcagtcc caagacata  aacacccaag acataaacac  10260
ccaacaggtc caccccgcct gctgcccagg cagagccgat tcaccaagac gggaattagg  10320
atagagaaag agtaagtcac acagagccgg ctgtgcggga aacggagtt  ctattatgac  10380 tcaaatcagt ctccccaagc attcggggat cagagttttt aaggataact tagtgtgtag  10440
ggggccagtg agttggagat gaaagcgtag ggagtcgaag gtgtccttt  gcgccgagtc  10500 agttcctggg tgggggccac aagatcggat gagccagttt atcaatccgg gggtgccagc  10560
tgatccatgg agtgcagggt ctgcaaaata tctcaagcac tgattgatct taggttttac  10620
aatagtgatg ttaccccagg aacaatttgg ggaaggtcag aatcttgtag cctgtagctg  10680
catgactcct aaaccataat ttcttttttg tttttttttt tttattttg  agacagggtc  10740 tcactctgtc acctaggctg gagtgcagtg gtgcaatcac agctcactgc agcctcaacg  10800
tcgtaagctc aagcgatcct cccacctcag cctgcctggt agctgagact acaagcgacg  10860
ccccagttaa ttttttgtatt tttggtagag cagcgtttt  gccgtgtggc cctggctggt  10920
ctcgaactcc tgggctcaag tgatccagcc tcagcctccc aaagtgctgg gacaaccggg  10980
gccagtcact gcacctggcc ctaaaccata atttctaatc ttttggctaa tttgttagtc  11040
ctacaaaggc agtctagtcc ccaggcaaaa aggggtttg  tttcgggaaa gggctgttac  11100
tgtctttgtt tcaaactata aactaagttc ctcctaaact tagttcggcc tacacccagg  11160
aatgaacaag gagagcttgg aggttagaag cacgatggaa ttggttaggt cagatctctt  11220
tcactgtctg agttataatt ttgcaatggt ggttcaaaga ctgcccgctt ctgacaccag  11280
tcgctgcatt aatgaatcgg ccaacgcgcg gggagaggcg gtttgcgtat tgggcgctct  11340
tccgcttcct cgctcactga ctcgctgcgc tcggtcgttc ggctgcggcg agcggtatca  11400
gctcactcaa aggcggtaat acggttatcc acagaatcag gggataacgc aggaaagaac  11460
atgtgagcaa aaggccagca aaaggccagg aaccgtaaaa aggccgcgtt gctggcgttt  11520
ttccataggc tccgccccc  tgacgagcat cacaaaaatc gacgctcaag tcagaggtgg  11580
cgaaacccga caggactata agataccag  gcgtttcccc ctggaagctc cctcgtgcgc  11640
```

```
tctcctgttc cgaccctgcc gcttaccgga tacctgtccg cctttctccc ttcgggaagc   11700
gtggcgcttt ctcatagctc acgctgtagg tatctcagtt cggtgtaggt cgttcgctcc   11760
aagctgggct gtgtgcacga acccccgtt  cagcccgacc gctgcgcctt atccggtaac   11820
tatcgtcttg agtccaaccc ggtaagacac gacttatcgc cactggcagc agccactggt   11880
aacaggatta gcagagcgag gtatgtaggc ggtgctacag agttcttgaa gtggtggcct   11940
aactacggct acactagaag aacagtattt ggtatctgcg ctctgctgaa gccagttacc   12000
ttcggaaaaa gagttggtag ctcttgatcc ggcaaacaaa ccaccgctgg tagcggtggt   12060 tttttgtt  gcaagcagca gattacgcgc agaaaaaaag gatctcaaga agatcctttg   12120
atcttttcta cggggtctga cgctcagtgg aacgaaaact cacgttaagg gattttggtc   12180
atgagattat caaaaaggat cttcacctag atccttttaa attaaaaatg aagttttaaa   12240
tcaatctaaa gtatatatga gtaaacttgg tctgacagtt accaatgctt aatcagtgag   12300
gcacctatct cagcgatctg tctatttcgt tcatccatag ttgcctgact ccccgtcgtg   12360
tagataacta cgatacggga gggcttacca tctggcccca gtgctgcaat gataccgcga   12420
gacccacgct caccggctcc agatttatca gcaataaacc agccagccgg aagggccgag   12480
cgcagaagtg gtcctgcaac tttatccgcc tccatccagt ctattaattg ttgccggaa   12540 gctagagtaa gtagttcgcc agttaatagt ttgcgcaacg ttgttgccat tgctacaggc   12600
atcgtggtgt cacgctcgtc gtttggtatg gcttcattca gctccggttc caacgatca   12660 aggcgagtta catgatcccc catgttgtgc aaaaaagcgg ttagctcctt cggtcctccg   12720
atcgttgtca gaagtaagtt ggccgcagtg ttatcactca tggttatggc agcactgcat   12780
aattctctta ctgtcatgcc atccgtaaga tgcttttctg tgactggtga gtactcaacc   12840
aagtcattct gagaatagtg tatgcggcga ccgagttgct cttgcccggc gtcaatacgg   12900
gataataccg cgccacatag cagaacttta aaagtgctca tcattggaaa acgttcttcg   12960
gggcgaaaac tctcaaggat cttaccgctg ttgagatcca gttcgatgta acccactcgt   13020
gcacccaact gatcttcagc atcttttact ttcaccagcg tttctgggtg agcaaaaaca   13080
ggaaggcaaa atgccgcaaa aaagggaata agggcgacac ggaaatgttg aatactcata   13140
ctcttccttt ttcaatatta ttgaagcatt tatcagggtt attgtctcat gagcggatac   13200
atatttgaat gtatttagaa aaataaacaa ataggggttc cgcgcacatt tccccgaaaa   13260
gtgccacctg acgtctaaga aaccattatt atcatgacat taacctataa aaataggcgt   13320
atcacgaggc cctttcgtct cgcgcgtttc ggtgatgacg gtgaaaacct ctgacacatg   13380
cagctcccgg agacggtcac agcttgtctg taagcggatg ccgggagcag acaagcccgt   13440
cagggcgcgt cagcgggtgt tggcgggtgt cggggctggc ttaactatgc ggcatcagag   13500
cagattgtac tgagagtgca ccatatgcgg tgtgaaatac cgcacagatg cgtaaggaga   13560
aaataccgca tcaggcgcca ttcgccattc aggctgcgca actgttggga agggcgatcg   13620
gtgcgggcct cttcgctatt acgccagggg aggcagagat tgcagtaagc tgagatcgca   13680
gcactgcact ccagcctggg cgacagagta agactctgtc tcaaaaataa aataaataaa   13740
tcaatcagat attccaatct tttccttat  ttatttattt attttctatt ttggaaacac   13800
agtccttcct tattccagaa ttacacatat attctatttt tctttatatg ctccagtttt   13860
ttttagacct tcacctgaaa tgtgtgtata caaaatctag gccagtccag cagagcctaa   13920
aggtaaaaaa taaataaata aaaataaat  aaaatctagc tcactccttc acatcaaaat   13980
ggagatacag ctgttagcat taaataccaa ataacccatc ttgtcctcaa taattttaag   14040
```

```
cgcctctctc caccacatct aactcctgtc aaaggcatgt gccccttccg ggcgctctgc    14100
tgtgctgcca accaactggc atgtggactc tgcagggtcc ctaactgcca agccccacag    14160
tgtgccctga ggctgcccct tccttctagc ggctgccccc actcggcttt gctttcccta    14220
gtttcagtta cttgcgttca gccaaggtct gaaactaggt gcgcacagag cggtaagact    14280
gcgagagaaa gagaccagct ttacagggggg tttatcacag tgcaccctga cagtcgtcag    14340
cctcacaggg ggtttatcac attgcaccct gacagtcgtc agcctcacag ggggtttatc    14400
acagtgcacc cttacaatca ttccatttga ttcacaattt ttttagtctc tactgtgcct    14460
aacttgtaag ttaaatttga tcagaggtgt gttcccagag gggaaaacag tatatacagg    14520
gttcagtact atcgcatttc aggcctccac ctgggtcttg aatgtgtcc cccgaggggt     14580 gatgactacc tcagttggat ctccacaggt cacagtgaca caagataacc aagacacctc    14640
ccaaggctac acaatgggc cgccctccac gtgcacatgg ccggaggaac tgccatgtcg     14700
gaggtgcaag cacacctgcg catcagagtc cttggtgtgg agggagggac cagcgcagct    14760
tccagccatc cacctgatga acagaaccta gggaaagccc cagttctact tacaccagga    14820
aaggc                                                               14825
```

<210> SEQ ID NO 3
<211> LENGTH: 9774
<212> TYPE: DNA
<213> ORGANISM: Artificial Sequence
<220> FEATURE:
<223> OTHER INFORMATION: Plasmid

<400> SEQUENCE: 3

```
tgggttaatt tactccaaga aaagacaaga gatccttgat ctgtgggtct ataacacaca      60
aggattcttc ccagattggc agaactacac accaggacca ggggttagat acccactgac     120
ctttgggtgg tgcttcaaac tagtaccaat ggatccagca gagatagaga aagccaatga     180
agaagagaac aactgtttat tacatcccat ctgccagcat ggaatggagg acgaagacag     240
agaagtgctg gtctggaagt ttgacagtcg cctggcactc aaacacatag ctcgagagaa     300
acatccggag ttttacaaag actgctgaca cagaagttgc tgacaaggga ctttccgctg     360
gggactttcc gagggaggtg tggtttggga ggagttgggg agtggctagc cctcagatgc     420
tgcatataag cagctgcttc tcgcctgtac tgggtctctc ttgctagacc agatttgagc     480
ctgggagctc tctggctagt agagaaccca ctgcttaagc ctcaataaag cttgccttga     540
gtgcttcaag tagtgtgtgc ccgtctgttg tgtgactctg gtaactagag atccctcaga     600
ccactttaga ctgtgtaaaa atctctagca gtggcgcccg aacagggact tgaagttaat     660
agggactcga aagcgaaagt tccagagaag atctctcgac gcacggactc ggcttgctga     720
ggtgcacaca gcaagaggcg agagcggcga ctggtgagta cgccaatttt tgactagcgg     780
aggctagaag gagagagatg ggtgcgagag cgtcagtgtt aagtggggga agattagatg     840
catgggagaa aattcggtta aggccagggg gaaagaaaaa atatagacta aaacatttag     900
tatgggcaag cagggagttg gaaagattcg cacttaaccc tggccttta gaaacagcag      960 aaggatgtca acaaataata gaacagttac aatcaactct caagacagga tcagaagaac    1020
ttaaatcatt atataatgca gtagcagtcc tttactgcgt acatcaaagg atagaggtaa    1080
aagacaccaa ggaagcttta gataaaatag gaggaactgca aaacaagagt aagcaaaaaa    1140
cacagcaggc agcagcaaag acacagcagg cagcagctgg cacaggatgc agccaaaatt    1200
```

```
accctatagt gcaaaatgca caagggcaaa tgacacacca gaatctgtca cctaggactt   1260
taaatgcatg ggtgaaggta atagaagaga aaggtttcag cccagaagta atacccatgt   1320
tctcagcatt atcagaggga gccaccccac aagatttaaa tatgatgcta aacatagtgg   1380
ggggacacca ggcagcaatg cagatgttga aagataccat caatgaggaa gctgcagaat   1440
gggacaggac acatccagta catgcagggc ctattccacc aggtcagatg agagaaccaa   1500
ggggaagtga catagcagga actactagta cccttcaaga acaaatgggc tggatgacaa   1560
gcaatccacc tatcccagtg ggagacatct ataaagatg gataatccta ggattaaata   1620
aaatagtaag aatgtatagc cctgtcagca tcttggacat aaaacaaggg ccaaaagaac   1680
cctttagaga ttatgtagat aggttcttta aaactttgag agctgaacaa gctacgcagg   1740
aggtaaaaaa ctggatgaca gaaaccttgc tggtccaaaa tgcaaatcca gactgtaagt   1800
ccattttaaa agcattagga gtaggggcca cattagaaga aatgatgaca gcatgccagg   1860
gagtaggagg acctggccat aaagcaaggg ttctggctga ggcaatgagt caagtacaac   1920
aggcaggagt aatgatgcag agaagcaatt ttaggggcca gagaacaata aagtgtttca   1980
actgtggcaa agaaggacac ctcgctagaa attgtaaggc ccctaggaaa agaggctgtt   2040
ggaaatgtgg gaaggaggga caccaaatga aagactgcac tgaaagacag gcgaattttt   2100
tagggagaat ctggccttcc agcaagggga ggccaggcaa ttttcctcag agcagaccag   2160
agccaacagc cccaccagca gagagcttgg ggatggggga agagatacc tcctccccga    2220 agcaggaacc gagggacaag gaactatacc ctccttagc ttccctcaaa tcactctttg   2280
gcaacgaccc ttagttacag taaaattagg gggacagctg atagaagcct tattagacac   2340
aggggcagat gatacagtat tagaagaaat agatttacca ggaaaatgga accaaaaat    2400 gatagggga attggaggtt ttatcaaagt aagacaatat gatcagatac ttatagaaat   2460
ttgtggaaaa aaggctatag gtacagtgtt agtaggacct acacctgtca acataattgg   2520
acgaaatatg ttgactcaga ttggttgcac tctaaatttc ccaattagtc ctattgaaac   2580
tgcaccagta aaactaaagc caggaatgga tggcccaaag gttaaacaat ggccattgac   2640
agaagaaaaa ataaaggcat taacagacat ttgtacagag atggaaaagg aagggaaaat   2700
ttcaaaaatt gggcctgaaa atccatacaa tactccagta tttgccataa agaaaaaga   2760 tagtactaaa tggagaaaat tagtcgactt cagagaactc aataaaagaa ctcaagactt   2820
ctgggaggtc caattaggaa tacctcatcc cgcgggatta aaaagaaaa aatcggtaac   2880 agtactagat gtgggggatg catatttttc agttcccctta gatgaagact ttagaaaata   2940
tactgcattc actatacca gtgtaaataa tgagacacca ggaattagat atcagtacaa   3000
tgtacttcca cagggatgga aaggatcacc agcaatattt caggctagca tgacaaaaat   3060
cttagagccc tttagaacag aaaatccaga gatagtgatt taccaatata tggatgattt   3120
atatgtagga tctgacttag atataggaca gcatagggca aaaatagaag agttaagaga   3180
acatctactg agatgggggt ttaccacacc agacaaaaaa catcagaaag aacctccatt   3240
cctttggatg ggatatgaac tccatcctga caaatggaca gtccagccca tacagctgcc   3300
agaaaaagac agctggactg tcaatgatat acagaaatta gtgggaaaac taaattgggc   3360
aagccagatt tatccaggaa ttaaagtaaa gcaactgtgt aaactcctca ggggagccaa   3420
agcactaaca gatataataa cactgactga ggaagcagaa ttagaattgg cagagaacag   3480
ggagattcta aaagaacctg tacatggagt ctattatgac ccagcaaaag gcctagtagc   3540
agaaatacag aagcaaggac aagaccaatg gacatatcaa atttatcaag agccatttaa   3600
```

```
aaatctaaaa acaggaaaat atgcaaaaaa gaggtctgct cacactaatg atgtaaaaca   3660
attaacagag gtagtgcaaa aagtggccac agaaagtgta gtaatatggg aaagacccc    3720 taaatttaga ctacccatac aaaaagaaac atgggaagca tggtggatgg agtattggca   3780
ggccacctgg attcctgaat gggagtttgt caatacccct cctctagtaa aattatggta   3840
ccagttagag aaagatccca tagtaggggc agaaactttc tatgtagatg ggcagctaa    3900 tagggaaact aagctaggaa aagcagggta tgtcactgac agaggaagac aaaaagttgt   3960
ctccataact gagacaacaa atcagaagac tgagttacat gcaatttatc tagccttgca   4020
ggattcagga tcagaagtaa atatagtaac agactcacag tatgcattag gaatcattca   4080
ggcacaacca gacaagagtg aatcagagtt agtcaatcta ataatagaga agctaataga   4140
aaaggacaaa gtctacctgt catgggtacc agcacacaaa ggaattggag gaaatgaaca   4200
agtagataaa ttagtcagta gtggagtcag gaaagtacta ttttagatg gcatagataa    4260 agcccaagaa gagcatgaaa aatatcacag caattggaga gcaatggcta gtgattttaa   4320
cctgccacct atagtagcaa agaaaatagt ggccagctgt gataaatgtc aactaaaagg   4380
ggaagccatg catggacaag tagactgtag tccaggaata tggcaattag attgtacaca   4440
tttagaagga aaaattatca tagtagcagt ccatgtagcc agtggctata tagaagcaga   4500
agttatccca gcagaaacag gacaggagac agcatacttt atattaaaat tagcaggaag   4560
atggccagtg aaagtaatac acacagataa tggcagtaat tttaccagtg ctgcagtaaa   4620
ggcagcatgt tggtgggcaa atgtcacaca agaatttgga attccctaca atccccaaag   4680
tcaaggagta gtagaatcta tgaataaaga attaagaaaa attatagggc aggtcaggga   4740
tcaagctgaa caccttaaga cagcagtaca gatggcagta ttcatccaca attttaaaag   4800 aaaaggggg attgggggt acagtgcagg ggagagaata atagacataa tagcatcaga    4860
catacaaact aaagaactac aaaaacaaat tatacaaatt caaaattttc gggtttatta   4920
cagggacagc agagatccaa tttggaaagg accagcaaaa ctactctgga aaggtgaagg   4980
ggcagtagta atacaggaca atagtgatat aaaggtagta ccaagaagaa aagcaaaaat   5040
cattagggat tatggaaaac agatggcagg taatgattgt gtggcaggta gacaggatga   5100
ggattagaac atggaacagt ttagtaaagc atcatatgta tgtctctaag aaagctggaa   5160
agtggtttta tagacatcac tatgaaagta gacatccaaa agtaagttca gaagtacaca   5220
ttccactagg agatgctaca ttggtaataa gaacatattg gggtctgcaa acaggagaaa   5280
gagactggca attgggtcat ggggtctcca tagaatggag actgagaaga tatagcacac   5340
aaatagatcc tgacctagca gaccaactaa ttcacctgca ttatttaac tgttttcag    5400 aatctgccat aaggagagcc atattaggac aagtagttag acctaggtgt gaatatcaag   5460
caggacataa tcaggtagga tctctacaat atttagcatt gaaagcatta gtaacaccaa   5520
caaggacaag gctaccttg cctagtgtta agaaattaac agaagacaga tggaacaagc    5580
cccagaagac caggggccac aaagggagcc gttcagtgaa tggacactag aattgttaga   5640
agagcttaaa catgaagctg ttagacattt tcctaggcca tggctccatg gattagggca   5700
acatatctac aacacatatg gggatacttg gaaggggtt ggagctataa taagaatgtt    5760
gcaataacta ctgtttgttc atttcagaat tgggtgccaa catagcagaa taggcattat   5820
tcgagggaga agaggcagga atggagctgg tagatcctaa cctagagccc tggaaacacc   5880
cgggaagtca gcctacaact gcttgtagca attgctattg taaaaagtgc tgctggcatt   5940
```

```
gccaattatg ctttctgaac aagggcttag gtatctccta tggcaggaag aagcggagac    6000
gccgacgagg aactcctcag agccgtcagg atcatcaaaa tcctgtacca aagcagtgag    6060
tagcaataat tagtatatgt gatgcaacct ttagaaatat ctgcaatagt aggactagta    6120
gtagctttca tagcagctgt agttgtgtgg accatagtat ttatagaata taggaaaata    6180
agaaaacaga agaaaataga taggttactt gaaagaataa aggaagagc agaagatagt     6240 ggcaatgaga gtgatgggga cacagaggaa ttatccaccc ttattgaggt gggtgactat    6300
catcttgtgg ataatcataa tttgtagtgc tgaaaagttg tgggttacag tatactatgg    6360
ggtaccggtg tggagagacg cagagaccac tctattttgt gcatcagagg ctagggcata    6420
tgatccagaa gcacataatg tctgggctac acatgcctgt gtacccacag accccaaccc    6480
acaagaatta cctttagaaa atgtaacaga agagtttaac atgtggaaaa ataacatggt    6540
agagcagatg catgaagata taattagtct atgggaccaa agcctaaagc catgtgtaaa    6600
gctaacccct ctctgcgtta cattaaattg ttctgacgtc accttcaaca gaacctttga    6660
tagtgaaatg aaaaaggaaa taaaaaactg cactttcaat acgaccacag aaagaataga    6720 taaaaagag aaagcatatg cacttttta taaacttgat ataaaagaac ttgagggaag     6780
taaggataat agtagtaata gtagccagtt tatactaata cattgtaata cctcgaccat    6840
tgcacaggct tgtccaaagg tgtcctttga gccaattccc atacattatt gtgccccagc    6900
tggttttgcg attctggagt gtaaagaaa gaatttcaat ggaacagggc catgcaagaa     6960
tgtcagtaca gtacaatgca cacatggaat caaaccagta gtgtcaactc aactgctact    7020
aaatggcagt ctagcagaag aagaggtaat gattagatct gaaaatatca aaacaatgc     7080 caaaaccata atagtacagc tggttactcc tgtaaaaatt aattgtacca gacctggcaa    7140
tcctataaga aaaagggtag gtataggacc aggacaagca ttccatgcaa caggtaatat    7200
aataggagac ataagacgag cacagtgtaa tgtcagtgga acagaatgga aggaagcttt    7260
acaaaaggta actgaacaat tagggaagca ctttaatgtt agcacaataa acttactaa     7320 atcctcagga ggggatgtag aaattacaac acatagttttt aattgtggag gagagttttt    7380
ctattgcaat acatcaggac tatttaatag cacttggagt aggaatagca ctgataacag    7440
cacttggaat atcaatgaca ctgtcagctc aaatcacaca ggaaatataa ctctccaatg    7500
cagaataagg caagttgtaa gaatgtggca gagggtagga caagcaatgt atgcccctcc    7560
catcccagga gaaattaagt gtaaatcaaa cattacagga atactattga caagagatgg    7620
agggacaaaa aatcagaatg caagtgagga atttaataca actgaggtat tcagacctgg    7680
aggaggagac atgagggaca attggagaag tgaattatat aaatataagg tagtacaaat    7740
tgaaccaata ggtgtggcac ccaccccgtgc aaaaagaaga gtggtgcaga agaaaaaag    7800 agcagttgga ctgggagctt tcttccttgg gttcttagga gttgcaggaa gcactatggg    7860
cgcagcgtca ataacgctga cggtacaggc cagacaatta ttgtctggta tagtgcaaca    7920
gcagagcaat ctgctgaagg ctatagaggc tcaacaacat atattgagac tcacggtctg    7980
gggcattaaa cagctccagg caagagtcct ggctctggaa agatacctaa aggatcaaca    8040
gctcctagga atttggggct gctctggaaa actcatctgc accactaatg tgccctggaa    8100
ctctagttgg agtaataaaa cttatgataa gatatgggac aatatgacct ggatgcaatg    8160
ggatagagaa attagcaatt acacagagat aatatatgat ctaattgaag aatcgcagaa    8220
gcagcaagaa aagaatgaac aagaattatt ggcattggac aagtgggaca gtctgtgaa     8280 ttggtttagc atatcaaact ggctatggta tataagaata ttcataatga tagtaggagg    8340
```

```
cttgataggc ttaagaatag tttgtgctgt gcttaatgta ataaatagag ttaggcaggg      8400
atactcacct ttgtcattcc agacccttac ccaccaccag agggaacccg acagacccga      8460
aagaatcgaa gaaggaggtg gcgagcgaga cagagacaga tccgtgcgct tagtgagcgg      8520
attcttagca cttgcctggg acgatctgag gagcctgtgc ctcttcagct accaccaatt      8580
gagagacttt gtattgattc tgggacacag cagtctcaag ggactgagac tggggtggga      8640
agcactcaaa cttctggggg atcttctgtt atactgggt cgggaactaa agaatagtgc       8700
tattaatttg cttgatacag tagcaatagc agtagctaac tggacagata gagttataga      8760
aatagggcaa agagttggta gagctattct aacatacct acaagaatca gacagggatt       8820
tgaaagggct ttgctataac atgggtggca agtggtcaaa agtagcata gtgggatggc       8880 ctcgggttag ggaagaatg agacaaaacc ctccagaagg ggttagggaa agaatgagac       8940
aaaaccctcc agcagcagca gaaggagtag gagcagcatc tcaagattta gctaaacatg      9000
gagcaatcac aagcagtaac acagcagaaa ctaatgctga ctgtgcctgg ctagaagcac      9060
aagagggaga ggaggtaggc tttccagtca ggccgcaagt acccttgaga ccaatgactt      9120
ataagggagc ttttgatctc agccactttt taaaagaaaa ggggggactg gatgggttaa      9180
tttactccaa gaaaaggcaa gagatccttg atctgtgggt ctataacaca caaggattct      9240
tcccagattg gcagaactac acaccaggac caggggttag atacccactg acctttgggt      9300
ggtgcttcaa actagtacca atggatccag cagagataga gaaagccaat gaagaagaga      9360
acaactgttt attacatccc atctgccagc atggaatgga ggacgaagac agagaagtgc      9420
tggtctggaa gtttgacagt cgcctggcac tcaaacacat agctcgagag aaacatccgg      9480
agttttacaa agactgctga cacagaagtt gctgacaagg gactttccgc tggggacttt      9540
ccgagggagg tgtggtttgg gaggagttgg ggagtggcta gccctcagat gctgcatata      9600
agcagccgct tctcgcttgt actgggtctc tcttgctaga ccagatttga gcctgggagc      9660
tctctggcta gtagagaacc cactgcttaa gcctcaataa agcttgcctt gagtgcttca      9720
agtagtgtgt gcccgtctgt tgtgtgactc tggttaacta gagatccctc agac            9774
```

<210> SEQ ID NO 4
<211> LENGTH: 12255
<212> TYPE: DNA
<213> ORGANISM: Artificial Sequence
<220> FEATURE:
<223> OTHER INFORMATION: Plasmid

<400> SEQUENCE: 4

```
gggtctctct ggttagacca gatctgagcc tgggagctct ctggctaact agggaaccca       60
ctgcttaagc ctcaataaag cttgccttga gtgcttcaag tagtgtgtgc ccgtctgttg      120
tgtgactctg gtaactagag atccctcaga cccttttagt cagtgtggaa aatctctagc      180
agtggcgccc gaacagggac atgaaagcga aaggaaaacc agaggagctc tctcgacgca      240
ggactcggct tgctgaagcg cgcacggcaa gaggcgaggg gcggcgactg gtgagtacgc      300
caaaaatttt gactagcgga ggctagaagg agagagatgg gtgcgagagc gtcagtatta      360 agcggggaa aattagatcg atgggaaaaa attcggttaa ggccagggggg aaagaaaaaa      420 tataaattaa acatatagt atgggcaagc agggagctag aacgattcgc agttaatcct       480
ggcctgttag aaacatcaga aggctgtaga caaatactgg gacagctaca accatccctt      540
cagacaggat cagaagaacg tagatcatta tataatacag tagcaaccct ctattgtgtg      600
```

```
catcaaagga tagagataaa agacaccaag gaagctttag acaagataga ggaagagcaa      660
aacaaaagta agaaaaaagc acagcaagca gcagctgaca caggacacag cagccaggtc      720
agccaaaatt accctatagt gcagaacatc caggggcaaa tggtacatca ggccatatca      780
cctagaactt taaatgcatg ggtaaaagta gtagaagaga aggctttcag cccagaagtg      840
atacccatgt tttcagcatt atcagaagga gccaccccac aagatttaaa caccatgcta      900
aacacagtgg ggggacatca agcagccatg caaatgttaa aagagaccat caatgaggaa      960
gctgcagaat gggatagagt gcatccagtg catgcagggc ctattgcacc aggccagatg     1020
agagaaccaa ggggaagtga catagcagga actactagta cccttcagga acaaatagga     1080
tggatgacac ataatccacc tatcccagta ggagaaatct ataaaagatg gataatcctg     1140
ggattaaata aaatagtaag aatgtatagc cctaccagca ttctggacat aagacaagga     1200
ccaaaggaac cctttagaga ctatgtagac cgattctata aaactctaag agccgagcaa     1260
gcttcacaag aggtaaaaaa ttggatgaca gaaaccttgt tggtccaaaa tgcgaaccca     1320
gattgtaaga ctattttaaa agcattggga ccaggagcga cactagaaga aatgatgaca     1380
gcatgtcagg gagtggggggg acccggccat aaagcaagag ttttggctga agcaatgagc     1440
caagtaacaa atccagctac cataatgata cagaaaggca ttttaggaa ccaaagaaag     1500 actgttaagt gtttcaattg tggcaaagaa gggcacatag ccaaaaattg cagggcccct     1560
aggaaaaagg gctgttggaa atgtggaaag gaaggacacc aaatgaaaga ttgtactgag     1620
agacaggcta atttttaagg gaagatctgg ccttcccaca agggaaggcc agggaatttt     1680
cttcagagca gaccagagcc aacagcccca ccagaagaga gcttcaggtt tggggaagag     1740
acaacaactc cctctcagaa gcaggagccg atagacaagg aactgtatcc tttagcttcc     1800
ctcagatcac tctttggcag cgacccctcg tcacaataaa gatagggggg caattaaagg     1860
aagctctatt agatacagga gcagatgata cagtattaga agaaatgaat ttgccaggaa     1920
gatggaaacc aaaaatgata gggggaattg gaggttttat caaagtaaga cagtatgatc     1980
agatactcat agaaatctgc ggacataaag ctataggtac agtattagta ggacctacac     2040
ctgtcaacat aattggaaga aatctgttga ctcagattgg ctgcacttta aattttccca     2100
ttagtcctat tgagactgta ccagtaaaat taaagccagg aatggatggc ccaaaagtta     2160
aacaatggcc attgacagaa gaaaaaataa aagcattagt agaaatttgt acagaaatgg     2220
aaaaggaagg aaaaatttca aaaattgggc ctgaaaatcc atacaatact ccagtatttg     2280
ccataaagaa aaaagacagt actaaatgga gaaaattagt agatttcaga gaacttaata     2340
agagaactca agatttctgg gaagttcaat taggaatacc acatcctgca gggttaaaac     2400
agaaaaaatc agtaacagta ctggatgtgg gcgatgcata ttttcagtt cccttagata     2460 aagacttcag gaagtatact gcatttacca tacctagtat aaacaatgag acaccaggga     2520
ttagatatca gtacaatgtg cttccacagg gatggaaagg atcaccagca atattccagt     2580
gtagcatgac aaaaatctta gagcctttta gaaaacaaaa tccagacata gtcatctatc     2640
aatacatgga tgatttgtat gtaggatctg acttagaaat agggcagcat agaacaaaaa     2700
tagaggaact gagacaacat ctgttgaggt ggggatttac cacaccagac aaaaaacatc     2760
agaaagaacc tccattcctt tggatgggtt atgaactcca tcctgataaa tggacagtac     2820
agcctatagt gctgccagaa aaggacagct ggactgtcaa tgacatacag aaattagtgg     2880
gaaaattgaa ttgggcaagt cagatttatg cagggattaa agtaaggcaa ttatgtaaac     2940
ttcttagggg aaccaaagca ctaacagaag tagtaccact aacagaagaa gcagagctag     3000
```

```
aactggcaga aaacagggag attctaaaag aaccggtaca tggagtgtat tatgacccat   3060
caaaagactt aatagcagaa atacagaagc aggggcaagg ccaatggaca tatcaaattt   3120
atcaagagcc atttaaaaat ctgaaaacag gaaagtatgc aagaatgaag ggtgcccaca   3180
ctaatgatgt gaaacaatta acagaggcag tacaaaaaat agccacagaa agcatagtaa   3240
tatggggaaa gactcctaaa tttaaattac ccatacaaaa ggaaacatgg gaagcatggt   3300
ggacagagta ttggcaagcc acctggattc ctgagtggga gtttgtcaat acccctccct   3360
tagtgaagtt atggtaccag ttagagaaag aacccataat aggagcagaa actttctatg   3420
tagatggggc agccaatagg gaaactaaat taggaaaagc aggatatgta actgacagag   3480
gaagacaaaa agttgtcccc ctaacggaca aacaaatca gaagactgag ttacaagcaa   3540
ttcatctagc tttgcaggat tcgggattag aagtaaacat agtgacagac tcacaatatg   3600
cattgggaat cattcaagca caaccagata agagtgaatc agagttagtc agtcaaataa   3660
tagagcagtt aataaaaaag gaaaaagtct acctggcatg ggtaccagca cacaaaggaa   3720
ttggaggaaa tgaacaagta gataaattgg tcagtgctgg aatcaggaaa gtactatttt   3780
tagatggaat agataaggcc caagaagaac atgagaaata tcacagtaat tggagagcaa   3840
tggctagtga ttttaaccta ccacctgtag tagcaaaaga aatagtagcc agctgtgata   3900
aatgtcagct aaaaggggaa gccatgcatg gacaagtaga ctgtagccca ggaatatggc   3960
agctagattg tacacattta gaaggaaaag ttatcttggt agcagttcat gtagccagtg   4020
gatatataga agcagaagta attccagcag agacagggca agaaacagca tacttcctct   4080
taaaattagc aggaagatgg ccagtaaaaa cagtacatac agacaatggc agcaatttca   4140
ccagtactac agttaaggcc gcctgttggt gggcggggat caagcaggaa tttggcattc   4200
cctacaatcc ccaaagtcaa ggagtaatag aatctatgaa taaagaatta agaaaaatta   4260
taggacaggt aagagatcag gctgaacatc ttaagacagc agtacaaatg gcagtattca   4320
tccacaattt taaaagaaaa ggggggattg ggggtacag tgcaggggaa agaatagtag   4380
acataatagc aacagacata caaactaaag aattacaaaa acaaattaca aaaattcaaa   4440
attttcgggt ttattacagg gacagcagag atccagtttg gaaaggacca gcaaagctcc   4500
tctggaaagg tgaaggggca gtagtaatac aagataatag tgacataaaa gtagtgccaa   4560
gaagaaaagc aaagatcatc agggattatg gaaaacagat ggcaggtgat gattgtgtgg   4620
caagtagaca ggatgaggat taacacatgg aaaagattag taaaacacca tatgtatatt   4680
tcaaggaaag ctaaggactg gttttataga catcactatg aaagtactaa tccaaaaata   4740
agttcagaag tacacatccc actagggga gctaaattag taataacaac atattggggt   4800
ctgcatacag gagaaagaga ctggcatttg ggtcagggga tctccataga atggaggaaa   4860
aagagatata gcacacaagt agaccctgac ctagcagacc aactaattca tctgcactat   4920
tttgattgtt tttcagaatc tgctataaga aataccatat taggacgtat agttagtcct   4980
aggtgtgaat atcaagcagg acataacaag gtaggatctc tacagtactt ggcactagca   5040
gcattaataa aaccaaaaca gataaagcca ccttttgccta gtgttaggaa actgacagag   5100
gacagatgga acaagcccca gaagaccaag ggccacagag ggagccatac aatgaatgga   5160
cactagagct tttagaggaa cttaagagtg aagctgttag acattttcct aggatatggc   5220
tccataactt aggacaacat atctatgaaa cttacgggga tacttgggca ggagtggaag   5280
ccataataag aattctgcaa caactgctgt ttatccattt cagaattggg tgtcgacata   5340
```

```
gcagaatagg cgttactcga cagaggagag caagaaatgg agccagtaga tcctagacta    5400
gagccctgga agcatccagg aagtcagcct aaaactgctt gtaccaattg ctattgtaaa    5460
aagtgttgct ttcattgcca agtttgcttc ataacaaaag gcttaggcat ctcctatggc    5520
aggaagaagc ggagacagcg acgaagacct cctcaaggca gtcagactca tcaagtttct    5580
ctatcaaagc agtaagtaat acatgtaatg caacctctac aaatagcaat agtagcatta    5640
gtagtagcaa taataatagc aatagttgtg tggtccatag taatcataga atataggaaa    5700
atattaagac aaagaaaaat agacaggtta attgatagac taatagaaag agcagaagac    5760
agtggcaatg agagtgaagg agaatatcaa gtcttatagc actgtggggg agatggggca    5820
ccatgctcct tgggatgttg atgatctgta gtgctacaga aaaattgtgg gtcacagtct    5880
attatggggt acctgtgtgg aagagaagca accaccactc tattttgtgc atcagatgct    5940
aaagcatatg atacagaggt acataatgtt tgggccacac atgcctgtgt acccacagac    6000
cccaacccac aagaagtaga attggaaaat gtgacagaaa attttaacat gtggaaaaat    6060
aacatggtag aacagatgca tgaggatata atcagtttat gggatcaaag cctaaagcca    6120
tgtgtaaaat taaccccact ctgtgttagt ttaaatggca ctgatttgaa actaatgata    6180
ctaataccaa tagtagtagc gggagaatga taatgggaaa ggagacatga aaaattgctc    6240
tttcaaaatc accacaaaca taagaggtaa ggtgcagaaa gaatatgcac ttttttataa    6300
acttgatata ataccaatag ataataatag taccagatat acgttgacaa gttgtaacac    6360
ctcagtcatt acacaggcct gtccaaaggt atcctttgag ccaattccca tacattattg    6420
tgccccggct ggttttgcga ttctaaaatg taataataag acgttcaatg gaaaaggacc    6480
atgttcaaat ggcagcacag tacaatgtac acatgggatt aggccagtag tatcaactca    6540
actgctgtta aatggcagtc tagcagaaga gaggtagta attagatccg aaaatttcgc    6600
ggacaatgct aaaaccataa tagtacagct gaacacatct gtagaaatta attgtacaag    6660
acccaacaac aatacaagaa aaaaaatcca gtatccagag gggaccaggg agagcatttg    6720
ttacaatagg agaaataata ggaataggac aagcacattg taacattagt agagcaaaat    6780
ggaatgccac ttacaataag atagctagca aattaagaga acaatttgga ataaaaacaa    6840
tatgctttaa gcatacctca ggaggggacc cagaaattgt aacgcacagt tttaattgtg    6900
gaggggaatt tttctactgt aattcaacac aactgtttaa tagtacttgg tttaatagta    6960
cttggagtac tgaagggtca aataacactg aaggaagtaa cacaatcaca ctcccatgca    7020
gaataaaaca atttataaac atgtggcagg aagtaggaaa agcaatgtat gcccctccca    7080
tcagcggaca aattagatgt tcatcaaata ttacagggct gctattaaca agagatggtg    7140
gtaataacaa caatggtccg agacttcaga cctggaggag gagatatgag gacaattgg     7200 agaagtgaat tatataaata taaagtagta aaaattgaac cattaggagt agcacccacc    7260
aaggcaaaga gaagagtggt gcagagagaa aaaagagcag tgggaatagg agctttgttc    7320
cttgggttct tgggagcagc aggaagcact atgggcgcag cgtcaatgac gctgacggta    7380
caggccagac aattattgtc tggtatagtg cagcagcaga acaatttgct gagggctatt    7440
gaggcgcaac agcatctgtt gcaactcaca gtctggggca tcaagcagct ccaggcaaga    7500
atcctggctg tggaaagata cctaaaggat caacagctcc tggggatttg gggttgctct    7560
ggaaaactca tttgcaccac tgctgtgcct tggaatgcta gttggagtaa taaatctctg    7620
gaacagattt ggaatcacac ggacctggat ggagtgggac agagaaatta acaattacac    7680
aagcttaata tatctcttaa ttgaagaatc gcaaaaccaa aagaaaaga atgaacaaga    7740
```

```
attattagaa ttagacaaat gggcaagttt gtggaattgg tttacataac aaaatggctg    7800
tggtatataa aattattcat aatgataata ggaggcttgg taggtttaag aatagttttt    7860
gctgtacttt ctgtagtgaa tagagttagg cagggatacc caccattatc gtttcagacc    7920
cacctccatg ccccgagggg acccgacagg cccgaaggaa tagaagaaga aggtggagag    7980
agagacagag acagatccat tcgattagtg aacggatcct tagcacttat ctgggacgat    8040
ctgcggagcc tgtgcctctt cagctaccac cgcttgagag acttactctt gattgtaacg    8100
aggattgtgg aacttctggg acgcaggggg tgggaagccc tcaaatattg gtggaatctc    8160
ctacaatatt ggagtcagga gctaaagaat agtgctgtta gcttgctcaa tgccacagct    8220
atagcagtag ctgaggggac ataggggtt atagaagtag tacaagaagc ttatagagct    8280
attcgccaca tacctagaag aataagacag ggcttggaaa ggattttgct ataagatggg    8340
tggcaagtgg tcaaaaagta gtgtggttgg atggcctgct gtaagggaaa gaatgagacg    8400
agctgagcca gcagcagatg gggtgggagc agcatctcga gacctagaaa acatggagc    8460 aatcacaagt agcaacacag cagctaacaa tgctgcttgt gcctggctag aagcacaaga    8520
ggaggagaag gtgggttttc cagtcacacc tcaggtacct ttaagaccaa tgacttacaa    8580
ggcagctgta gatcttagcc acttttaaa agaaaagggg ggactggaag gctaattca    8640 ctcccaacga agacaagata tccttgatct gtggatctac cacacacaag gctacttccc    8700
tgattggcag aactacacac caggaccagg gatcagatat ccactgacct ttggatggcg    8760
ctacaagcta gtaccagttg agccagagaa gttagaagaa gccaacaaag gagagaacac    8820
cagcttgtta caccctgtga gcctgcatgg aatggatgac ccggagagag aagtgttaga    8880
gtggaggttt gacagccgcc tagcatttca tcacgtggcc cgagagctgc atccggagta    8940
cttcaagaac tgctgatatc gagcttgcta caagggactt tccgctgggg actttccagg    9000
gaggcgtggc ctgggcggga ctggggagtg cgagccctc agatcctgca tataagcagc    9060 tgcttttttgc ctgtactggg tctctctggt tagaccagat ctgagcctgg gagctctctg    9120
gctaactagg gaacccactg cttaagcctc aataaagctt gccttgagtg cttcaagtag    9180
tgtgtgcccg tctgttgtgt gactctggta actagagatc cctcagaccc ttttagtcag    9240
tgtggaaaat ctctagcagt cacgtaactc tgaaaaggtc aaagatattg atgcttgata    9300
cagaaggaag ggaataccag tgagttgtct ggactacact aaacataccct gaaatctgag    9360 ttcgagaagt ataatagaac tggactccaa attaagtctc agttgcaaac tggattaatg    9420
ggggatagat ttctatctag agggggcag gtgaccttca gaccttggca ctggaggtgg    9480
cccggcagaa gcgcggcatc gtggatcagt gctgcaccag catctgctct ctctaccaac    9540
tggagaacta ctgcaactag gcccaccact accctgtcca cccctctgca atgaataaaa    9600
cctttgaaag agcactacaa gttgtgtgta catgcgtgca tgtgcatatg tggtgcgggg    9660
ggaacatgag tggggctggc tggagtgcg atgataagct gtcaaacatg agaattcttg    9720
aagacgaaag ggcctcgtga tacgcctatt tttataggtt aatgtcatga taataatggt    9780
ttcttagacg tcaggtggca cttttcgggg aaatgtgcgc ggaaccccta tttgttatt    9840 tttctaaata cattcaaata tgtatccgct catgagacaa taaccctgat aaatgcttca    9900
ataatattga aaaggaaga gtatgagtat tcaacatttc cgtgtcgccc ttattccctt    9960
ttttgcggca ttttgccttc ctgtttttgc tcacccagaa acgctggtga agtaaaaga   10020 tgctgaagat cagttgggtg cacgagtggg ttacatcgaa ctggatctca acagcggtaa   10080
```

```
gatccttgag agttttcgcc ccgaagaacg ttttccaatg atgagcactt ttaaagttct   10140
gctatgtggc gcggtattat cccgtgttga cgccgggcaa gagcaactcg gtcgccgcat   10200
acactattct cagaatgact tggttgagta ctcaccagtc acagaaaagc atcttacgga   10260
tggcatgaca gtaagagaat tatgcagtgc tgccataacc atgagtgata acactgcggc   10320
caacttactt ctgacaacga tcggaggacc gaaggagcta accgcttttt tgcacaacat   10380
gggggatcat gtaactcgcc ttgatcgttg ggaaccggag ctgaatgaag ccataccaaa   10440
cgacgagcgt gacaccacga tgcctgcagc aatggcaaca cgttgcgca aactattaac    10500 tggcgaacta cttactctag cttcccggca acaattaata gactggatgg aggcggataa   10560
agttgcagga ccacttctgc gctcggccct tccggctggc tggtttattg ctgataaatc   10620
tggagccggt gagcgtgggt ctcgcggtat cattgcagca ctggggccag atggtaagcc   10680
ctcccgtatc gtagttatct acacgacggg gagtcaggca actatggatg aacgaaatag   10740
acagatcgct gagataggtg cctcactgat taagcattgg taactgtcag accaagttta   10800
ctcatatata ctttagattg atttaaaact catttttaa tttaaaagga tctaggctgc    10860
tgcttgcaaa caaaaaaacc accgctacca gcggtggttt gtttgccgga tcaagagcta   10920
ccaactcttt ttccgaaggt aactggcttc agcagagcgc agataccaaa tactgtcctt   10980
ctagtgtagc cgtagttagg ccaccacttc aagaactctg tagcaccgcc tacatacctc   11040
gctctgctaa tcctgttacc agtggctgct gccagtggcg ataagtcgtg tcttaccggg   11100
ttggactcaa gacgatagtt accggataag gcgcagcggt cgggctgaac ggggggttcg   11160
tgcacacagc ccagcttgga gcgaacgacc tacaccgaac tgagatacct acagcgtgag   11220
ctatgagaaa gcgccacgct tcccgaaggg agaaaggcgg acaggtatcc ggtaagcggc   11280
agggtcggaa caggagagcg cacgagggag cttccagggg gaaacgcctg gtatctttat   11340
agtcctgtcg ggtttcgcca cctctgactt gagcgtcgat ttttgtgatg ctcgtcaggg   11400
gggcggagcc tatggaaaaa cgccagcaac ggagatgcgc cgcgtgcggc tgctggagat   11460
ggcggacgcg atggatatgt tctgccaagg gttggtttgc gcattcacag ttctccgcaa   11520
gaattgattg gctccaattc ttggagtggt gaatccgtta gcgaggtgcc gccggcttcc   11580
attcaggtcg aggtggcccg gctccatgca ccgcgacgca acgcggggag gcagacaagg   11640
tatagggcgg cgcctacaat ccatgccaac ccgttccatg tgctcgccga ggcggcataa   11700
atcgccgtga cgatcagcgg tccaatgatc gaagttaggc tggtaagagc cgcgagcgat   11760
ccttgaagct gtccctgatg gtcgtcatct acctgcctgg acagcatggc ctgcaacgcg   11820
ggcatcccga tgccgccgga agcgagaaga atcataatgg ggaaggccat ccagcctcgc   11880 gtcgggagc ttttttgcaaa agcctaggcc tccaaaaaag cctcctcact acttctggaa    11940
tagctcagag gccgaggcgg cctcggcctc tgcataaata aaaaaattta gtcagccatg   12000
gggcggagaa tgggcggaac tgggcggagt taggggcggg atgggcggag ttaggggcgg   12060
gactatggtt gctgactaat tgagatgcat gttcgaatcg cgaccgcggt ccggagtact   12120
tcaagaactg ctgatatcga gcttgctaca agggactttc cgctggggac tttccaggga   12180
ggcgtggcct gggcgggact ggggagtggc gagccctcag atcctgcata taagcagctg   12240
ctttttgcct gtact                                                    12255
```

THERAPEUTIC COMPOSITION OF CAMEL MILK

The Applicant hereby incorporates by reference the sequence listing contained in the ASCII text file titled 32490.44_Sequence_Listing_ST25, created on Jul. 3, 2017, and having 64 KB of data.

CROSS-REFERENCE TO RELATED APPLICATIONS

This application claims the benefit of South African Patent Application No. 2016/07084, filed on Oct. 14, 2016.

BACKGROUND OF THE INVENTION

1. Field of the Invention

A therapeutic composition of camel milk relates to a composition useful for medical treatment, and particularly, to a composition useful for the treatment of HIV/AIDS.

2. Description of the Related Art

Infection with Human Immunodeficiency Virus (HIV), a pathogenic retrovirus, can cause Acquired Immunodeficiency Syndrome (AIDS). AIDS is a major global health emergency, and is the sixth leading cause of early death in the world and the third in low-income countries. AIDS is considered an important cause of morbidity and mortality among young people. Moreover, it has reduced the life expectancy at birth in the African continent to 49 years from 53 years.

AIDS was first recognized in the United States in 1981 and has become one of the biggest problems facing the world today. A total of 36.9 million people were infected by HIV by the end of 2014. It has also been observed that the annual rate of new infection with HIV in the entire human population is not declining as 2 million people became newly infected with HIV in 2014 globally.

There are more than 21 million people who died from AIDS in the last decade. Although the rate of death due to AIDS has begun to drop in some nations, by an annualized rate of 2.8% between 2000 and 2013 as in the United States, primarily through the recent use of combination drug therapies against HIV infection and/or through the strict religious and moral codes. However, it is estimated that 16,000 people worldwide are being infected daily with HIV. Treatment success also has been limited by poor tolerance of the treatments by patients and the emergence of resistant strains of HIV. Thus, a need exists for an effective HIV treatment that is well tolerated, relatively inexpensive, and easily accessible.

Although great efforts have been dedicated to effective remedial and preventive methods for many years, there is no working vaccine or cure for HIV/AIDS yet. An ideal vaccine should be innocuous and capable of inducing neutralizing antibodies as well as persistent immune responses in the mucous membrane and blood. Many HIV vaccines currently developed in the world are still in the stages of animal trials. Although vaccines against HIV membrane proteins gp160 and gp120 have already moved into first, second, or third stages of clinical trials, the results of the trials are disappointing. Moreover, many vaccines that are effective to prevent HIV infection in small laboratory animals are not necessarily effective in humans. Although the subsequent or the second generation DNA vaccines seem to influence towards both humoral and cellular immune responses regardless of animal models used, researchers suggested that new modified DNA vaccines can be more efficient by broadly activate CD8+ cytotoxic T lymphocytes (CTLs) in larger animal models, compared with previous approved DNA methods. The fact that scientists are making little progress in HIV vaccine research could be attributed to the complexity and variability of HIV genetic materials. Although the use of combination drug therapies against HIV has proven to be effective in many patients, the current drug regimens are far from ideal due to several drawbacks and side effects documented in the literature.

Currently novel therapeutic approaches are being investigated at an encouraging rate and have the potential to improve the odds against the virus. Among them, immunotherapeutic approaches are one of the exciting areas and can be considered as adjunct to combined antiretroviral therapy for improving immune competence and can provide a sustained control of HIV replication.

Understanding the immune responses against HIV infection is essential for immunotherapy and the treatment of HIV/AIDS. Immunotherapy is meant to help the natural immune system in accomplishing control over viral infection. Different immunotherapy configurations have been assessed in either therapy-naive or therapy-experienced HIV-tainted patients throughout the last 20 years. These arrangements or configurations included non-antigen specific approaches, for example, cytokines that invigorate immunity or stifle the viral replication, and additionally antibodies that piece negative regulatory pathways. Various HIV-specific therapeutic vaccinations have additionally been proposed, utilizing inactivated virus in vivo, plasmid DNA encoding HIV antigens, or recombinant viral vectors containing HIV genes. These findings may give an objective and rational for immunotherapy in persons with progressive infection and have inspired an expanding effort to develop new strategies to enhance immunity.

Thus, a therapeutic composition solving the aforementioned problems is desired.

SUMMARY OF THE INVENTION

A therapeutic composition of camel milk can include an herbal composition having solid material or liquid extracts from the solid material of at least one of *Saussurea acrophila* Diels, *Saussurea ceratocarpa*, and *Aucklandia lappa* Decne. The solid material may include one or more of parts or the whole of the stem, the bark, the flowers and the roots of one or more, but preferably all of *Saussurea acrophila* Diels, *Saussurea ceratocarpa*, and *Aucklandia lappa* Decne. The therapeutic composition can include camel milk. The camel milk can include camel's milk having anti-HIV antibodies therein (HIV immunized camel milk). The therapeutic composition can include the herbal composition mixed with the camel milk to provide a treated camel milk. The HIV immunized camel milk can be obtained from a camel immunized against HIV. The camel can be immunized against HIV by administering to the camel the modified DNA plasmids of SEQ. ID No.: 3 and SEQ ID No.: 4.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
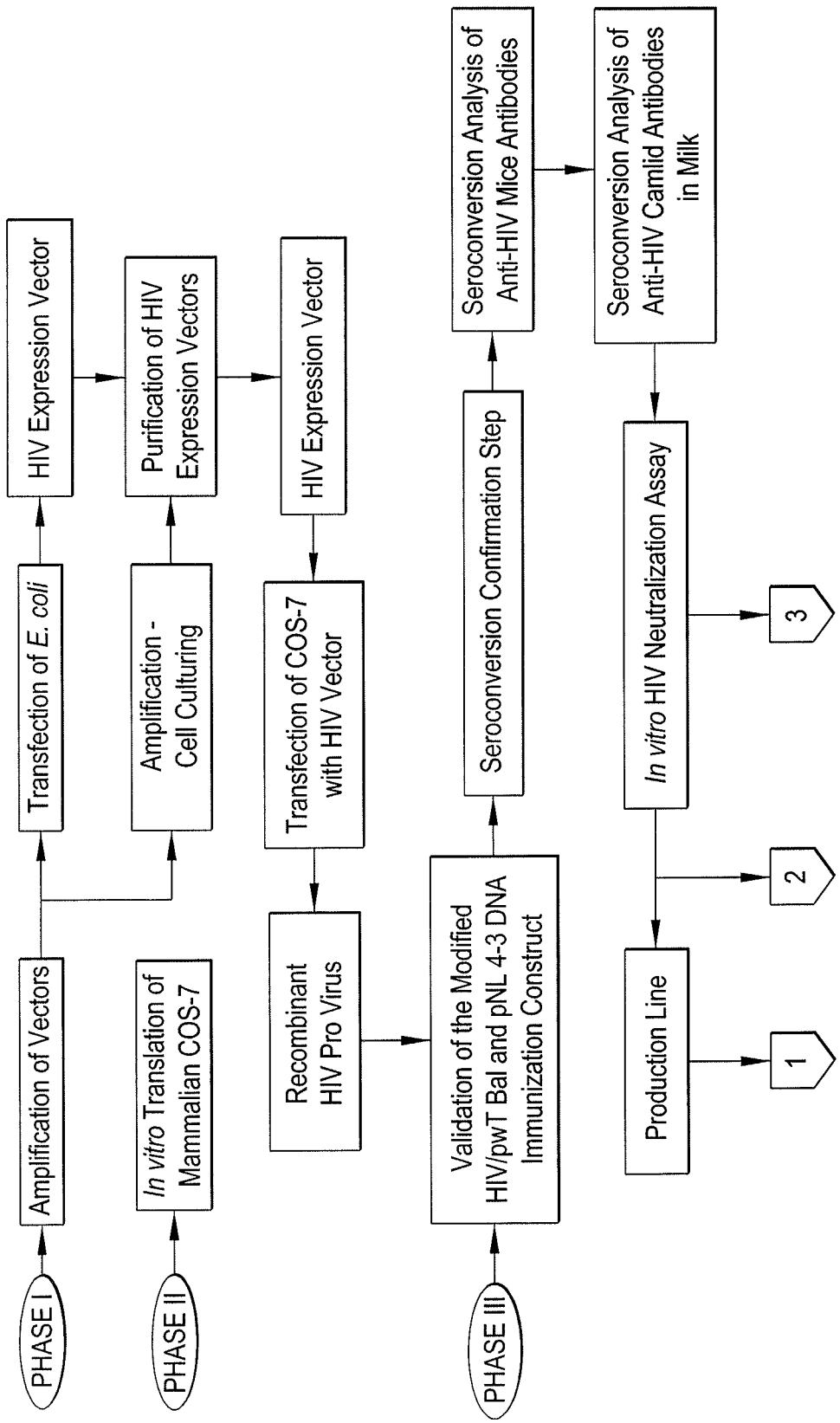
FIG. 1A is a flowchart showing the steps by which expression vectors were developed, tested, and demonstrated to produce seroconversion in camels.
Figure 1B:
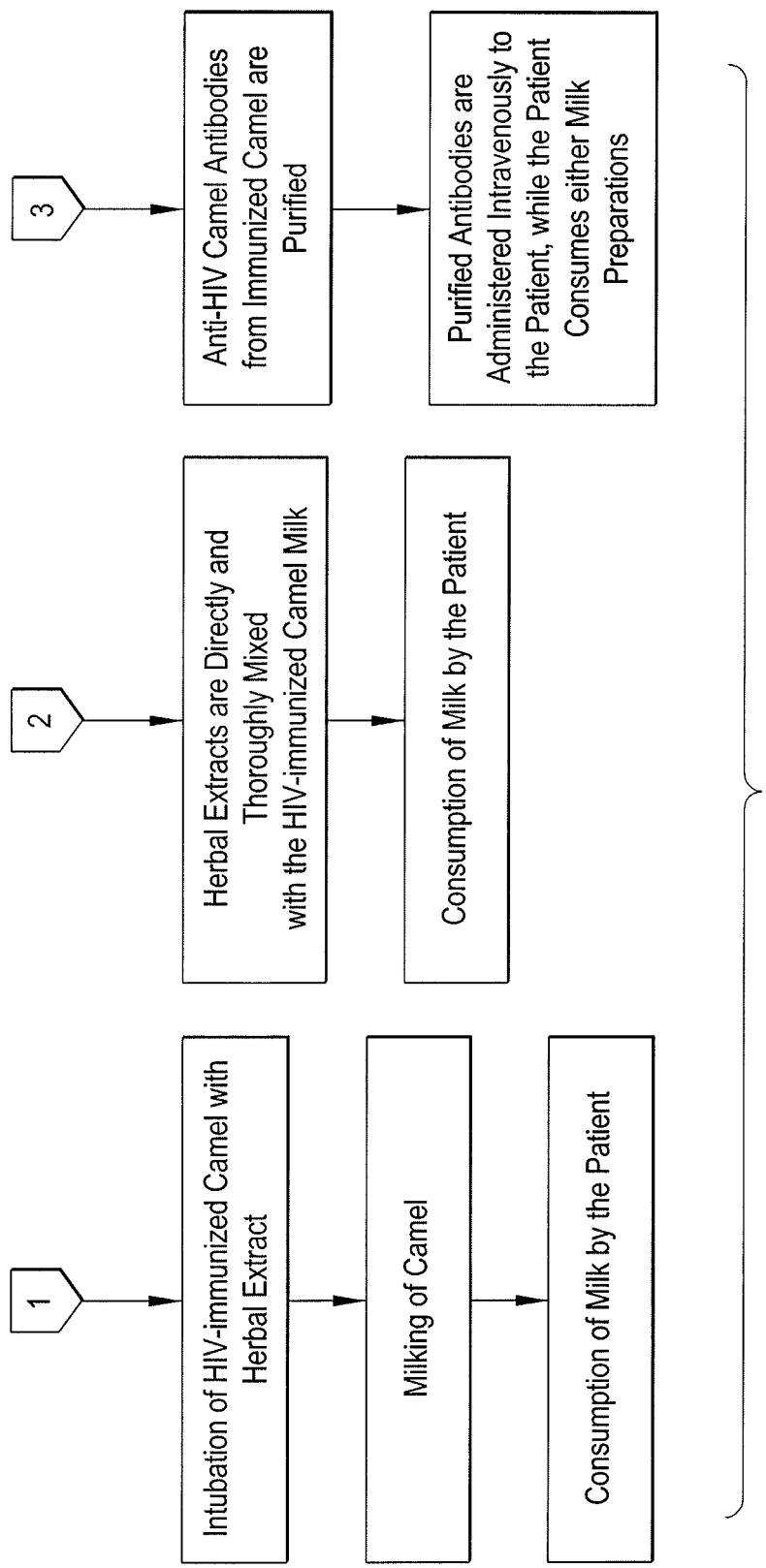
FIG. 1B is a continued flowchart showing steps by which different combination HIV/AIDS therapies of formulated camel milk may be produced.
Figure 2:
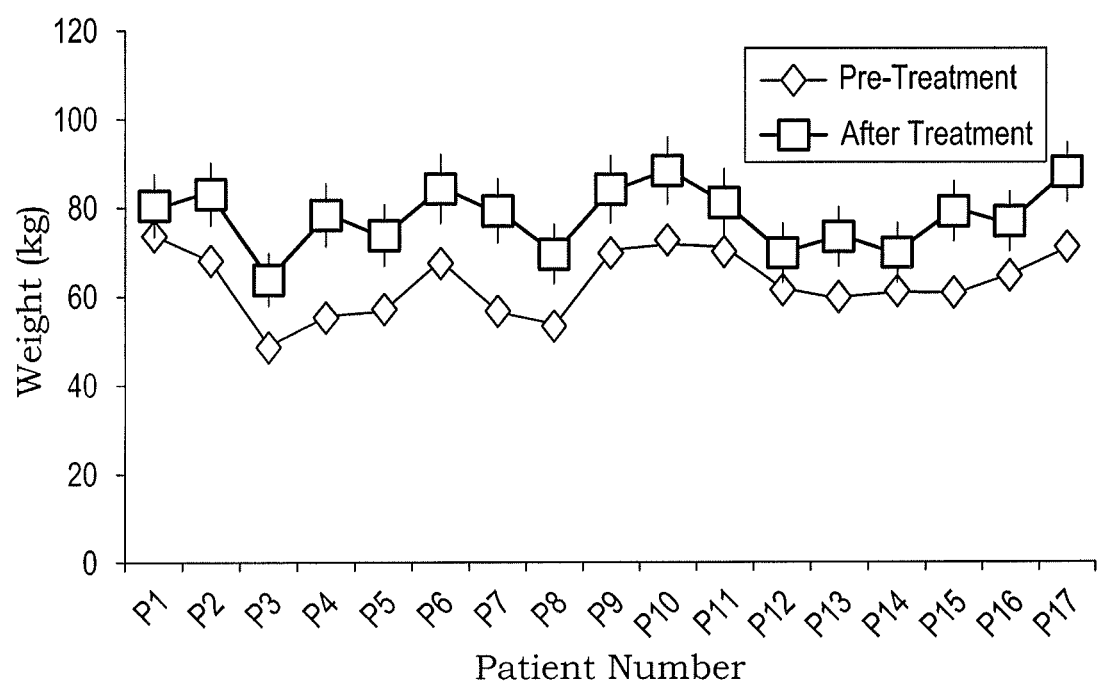
FIG. 2 is a graph showing pre-treatment and post-treatment weights for all seventeen patients treated with the treated milk.

A therapeutic composition of camel milk can include an herbal composition having solid material or liquid extracts from the solid material of at least one of *Saussurea acrophila* Diels, *Saussurea ceratocarpa*, and *Aucklandia lappa* Decne. The solid material may include one or more of parts or the whole of the stem, the bark, the flowers and the roots of one or more, but preferably all of *Saussurea acrophila* Diels, *Saussurea ceratocarpa*, and *Aucklandia lappa* Decne. For example, the solid material may include parts or the whole of the stem and the bark of *Saussurea acrophila* Diels and *Saussurea ceratocarpa*, and parts or the whole of the roots of *Aucklandia lappa* Decne. The solid material may be in finely divided particulate form and may be dry or wet, e.g. in suspension. The composition may include a mixture of solid material of two or more of *Saussurea acrophila* Diels, *Saussurea ceratocarpa*, and *Aucklandia lappa* Decne.

The therapeutic composition can include camel milk. The camel milk can include camel's milk having anti-HIV antibodies therein (HIV-immunized camel milk). The therapeutic composition can include treated camel's milk. The treated camel's milk can include a mixture of camel milk and the herbal composition. The treated camel's milk can include a concentration of about 800 g of the herbal composition per 5-6 liters of the camel milk.

The liquid extract may include liquid solvent extracts from the solid material of one or more, but preferably all of *Saussurea acrophila* Diels, *Saussurea ceratocarpa*, and *Aucklandia lappa* Decne. The extracts may be obtained by treatment of solid material of *Saussurea acrophila* Diels, *Saussurea ceratocarpa*, and *Aucklandia lappa* Decne with a solvent. The solvent may be ethanol. The ethanol may be about 96% ethanol, more preferably 99.9% ethanol. In the case of the composition comprising liquid extracts, the composition may comprise a mixture of liquid solvent extracts from solid material of two or more of *Saussurea acrophila* Diels, *Saussurea ceratocarpa*, and *Aucklandia lappa* Decne.

The solid material may comprise one or more of parts or the whole of the stem, the bark, the flowers and the roots of one or more but preferably all of *Saussurea acrophila* Diels, *Saussurea ceratocarpa*, and *Aucklandia lappa* Decne. More preferably, the solid material may comprise parts or the whole of the stem and the bark of *Saussurea acrophila* Diels, *Saussurea ceratocarpa*, and *Aucklandia lappa* Decne, and parts or the whole of the roots of *Aucklandia lappa* Decne. The solid material can be previously harvested. The harvested material can be formed into finely divided particulate, e.g., powdered, form, e.g., by grinding.

On a dry basis, the herbal composition may comprise from about 10-20% by weight, preferably 14% by weight, of the solid material of *Saussurea acrophila* Diels or liquid extract thereof, from about 10-20% by weight, preferably 14% by weight, of the solid material of *Saussurea ceratocarpa* or liquid extract thereof and about 45-75% by weight, preferably 72% by weight, of the solid material of *Aucklandia lappa* Decne or liquid extract thereof.

The herbal composition may be provided in an aqueous form for use, particularly for use as a medicament. The aqueous form may, for example, comprise from about 0.5 g to about 1 g, preferably about 0.8 g of extract per ml water, i.e. preferably 800 g of extract per liter of water. Of the 800 g of extract, about 112 g is extract of *Saussurea acrophila* Diels, about 112 g is extract of *Saussurea ceratocarpa*, and about 576 g is extract of *Aucklandia lappa* Decne. The water is preferably distilled water. The quantity can be scaled-up according to the requirements of a subject to which it is to be administered, or to the need of the manufacturer.

An effective amount of the therapeutic composition can be administered to a patient in need thereof for medical treatment. The medical treatment can include treatment of human immunodeficiency virus (HIV), HIV/AIDS or prevention of HIV infection. The medical treatment can include treatment for or prevention of any one or more of viral infections, including, but not limited to Epstein Barr virus, Herpes simplex, Herpes zoster, influenza, and cancer. The medical treatment can include administering to a patient in need thereof an effective amount of treated camel milk. The treated camel milk can include about 6.8 g of extract of *Saussurea acrophila* Diels, about 6.8 g of extract of *Saussurea ceratocarpa*, about 34.6 g of extract of *Aucklandia lappa* Decne, and about 300 ml of camel milk.

The composition need not strictly comprise the liquid extracts. It may, in one embodiment, comprise an emulsion or a mixture of solid material of *Saussurea acrophila* Diels, *Saussurea ceratocarpa*, and *Aucklandia lappa* Decne.

For commercial and industrialized purposes the composition can be further processed by spray-drying, or other similar drying techniques, and subsequent granulation thereof into particles which can be further encapsulated, tableted or filled into sachets or blister packets as required.

The method of preparing the composition may include combining the solid material of at least one but preferably all of *Saussurea acrophila* Diels, *Saussurea ceratocarpa*, and *Aucklandia lappa* Decne. The method may include forming a mixture of solid material of at least one but preferably all of *Saussurea acrophila* Diels, *Saussurea ceratocarpa*, and *Aucklandia lappa* Decne. The method may include a prior step of harvesting the solid material. The method may include another prior step of forming the harvested solid material into finely divided particulate, powdered, form, e.g. by grinding. Thus, the composition of solid material may be one or a mixture of the harvested solid material in finely divided particulate form.

A composition comprising liquid extracts from solid material of at least one of *Saussurea acrophila* Diels, *Saussurea ceratocarpa*, and *Aucklandia lappa* Decne can be prepared by forming a mixture of liquid extracts from solid material of at least one of *Saussurea acrophila* Diels, *Saussurea ceratocarpa*, and *Aucklandia lappa* Decne. This method may include preparing the liquid extracts by treating solid material of at least one of *Saussurea acrophila* Diels, *Saussurea ceratocarpa*, and *Aucklandia lappa* Decne with a solvent. The solvent may be ethanol, typically about 96% ethanol, or about 99.9% ethanol.

The solid material used to produce the liquid extracts may comprise one or more of parts or the whole of the stem, the bark, the flowers and the roots of one or more but preferably all of *Saussurea acrophila* Diels, *Saussurea ceratocarpa*, and *Aucklandia lappa* Decne. The solid material may comprise parts or the whole of the stem and the bark of

*Saussurea acrophila* Diels and *Saussurea ceratocarpa*, and parts or the whole of the roots of *Aucklandia lappa* Decne.

Treatment of the solid material with the solvent may be in a mass ratio of 2:1 solvent:material, particularly when the solvent is ethanol.

The liquid extracts may be individually prepared by treating the solid material of one or more of *Saussurea acrophila* Diels, *Saussurea ceratocarpa*, and *Aucklandia lappa* Decne separately. The composition may then comprise one of the extracts, or may be prepared by mixing two or more of the extracts.

The liquid extracts may be prepared as a combination of extracts, by preparing a mixture of solid material of two or more of *Saussurea acrophila* Diels, *Saussurea ceratocarpa*, and *Aucklandia lappa* Decne and treating the mixture of solid material with the solvent. On a dry basis, the mixture may comprise from about 10-20% by weight, or about 14% by weight, of the solid material of *Saussurea acrophila* Diels, from about 10-20% by weight, or about 14% by weight, of the solid material of *Saussurea ceratocarpa* and about 45-75% by weight, or about 72% by weight, of the solid material of *Aucklandia lappa* Decne.

The therapeutic composition can include a medicament or a precursor to a medicament. The medicament may be treated camel's milk or HIV-immunized camel's milk, i.e., camel's milk obtained from a camel that was immunized using modified DNA inserts of HIV pWT/BaL (SEQ ID NO.: 3) and HIV pNL4-3 (SEQ ID NO.: 4). The HIV-immunized may include milk obtained from a camel that is caused to digest the herbal composition which comprises solid material or liquid extracts of solid material from one or more of *Saussurea acrophila* Diels, *Saussurea ceratocarpa*, and *Aucklandia lappa* Decne, and immunized using modified DNA inserts of HIV pWT/BaL (SEQ ID NO.: 3) and HIV pNL4-3 (SEQ ID NO.: 4). This may be accomplished by supplementing the camel's feed, or by intubating the camel with 500-1000 g, preferably 800 g, of the solid material or liquid extracts of solid material from one or more of *Saussurea acrophila* Diels, *Saussurea ceratocarpa*, and *Aucklandia lappa* Decne. Preferably, immunization occurs prior to causing the camel to digest the herbal composition. About 300 ml of the HIV-immunized camel's milk can be administered to a patient in need thereof three times a day.

The immunized camel's milk may include anti-HIV heavy chain IgG antibodies (hcIgG). hcIgG antibodies are rare, small antibodies, known to be produced by camels. These antibodies have unique features due to their smaller size, the absence of heavy chain constant regions, and the complete absence of the light chain. Due to their smaller size and unique features, hcIgG antibodies may possess improved bioactivity when compared with normal IgG antibodies.

The therapeutic composition may be used in medical treatment, by administering it to a person in need thereof. The therapeutic composition can be processed and formulated in a form suitable for oral, parenteral, or intravenous administration to a patient.

The medical treatment may be medical treatment for treatment of HIV/AIDS or prevention of human immunodeficiency virus (HIV) infection.

The medical treatment may also be medical treatment for treatment or prevention of any one or more of viral infections including but not limited to Epstein Barr virus, Herpes simplex, Herpes zoster, influenza, and cancer.

The treated camel's milk can be formed by mixing the solid material or liquid extracts of solid material from one or more of *Saussurea acrophila* Diels, *Saussurea ceratocarpa*, and *Aucklandia lappa* Decne. The treated camel's milk may comprise a concentration of about 800 g of the solid material or liquid extracts of solid material from one or more of *Saussurea acrophila* Diels, *Saussurea ceratocarpa*, and *Aucklandia lappa* Decne, per about 5-6 liters of the camel's milk. Other concentrations may also find application.

The medical treatment may involve administering the treated camel's milk to a subject in need thereof. The treated camel's milk can be prepared by mixing about 6.8 g of extract of *Saussurea acrophila* Diels, about 6.8 g of extract of *Saussurea ceratocarpa*, and about 34.6 g of extract of *Aucklandia lappa* Decne with about 300 ml camel's milk. The medical treatment may include administering 300 ml of the treated camel's milk to a subject three times a day.

The dosage of the compositions of the invention to be ingested will vary, depending on factors such as severity of the conditions, age, physical condition and body weight of the patient, diet, etc. Subjects may vary considerably depending on the factors indicated above. However, one benefit of the composition of the present invention is that the dosage is not "critical" since the edible compositions of the present invention are holistic in nature and represent dietary supplements in their own right, "over dosing" is not a problem. The individual patient with a particular body weight and life style may readily determine the proper dosage by starting out the general dosage.

As a general guide, it is expected that a camel with a body weight in the range of about 600 to about 1000 Kg would ingest about 500-1000 g/day of the solid material or liquid extracts from the solid material of at least one of *Saussurea acrophila* Diels, *Saussurea ceratocarpa*, and *Aucklandia lappa* Decne. Typically, a camel would ingest about 0.18 g of the solid material or liquid extracts from the solid material of at least one of *Saussurea acrophila* Diels, *Saussurea ceratocarpa*, and *Aucklandia lappa* Decne per Kg of body weight. It is to be understood that these consumption amounts are only general guides and the proper amounts for individual camels may vary. The amount ingested by a camel has been found to be most effective when administered at a dosage of about 750 g per day, with an effective range of about 500-800 g per day. This is based on a pilot study where a subject is administered about 300 ml of the medicament or HIV-immunized camel's milk three times a day, in which case the camel was intubated with about 800 g of the solid material or liquid extracts from the solid material of at least one of *Saussurea acrophila* Diels, *Saussurea ceratocarpa*, and *Aucklandia lappa* Decne per day. However, it will be appreciated that subjects may be given a higher dosage according to their status and life style with no expected harm or side effects that may result.

The intubated solution administered to the camel may comprise an ethanolic extract of the stem/bark of *Saussurea acrophila* Diels and *Saussurea ceratocarpa* in the range of about 10-20% respectively, and preferably about 14% respectively, in water. The intubated solution administered to the camel may further comprise an aqueous extract of the root of *Aucklandia lappa* Decne in the range of about 45%-75%, and preferably about 72% in water.

Example 1

Method of Preparing Pharmaceutical Compositions

The stem and bark of *Saussurea acrophila* Diels and *Saussurea ceratocarpa*, and the root of *Aucklandia lappa*

Decne were harvested, weighed and thoroughly washed in cold water to remove any dirt, soil and other undesirable contaminants.

The washed, harvested material was pre-treated with distilled or de-ionized water in an about 16:1 dry weight ratio of water:harvested material and subsequently dried in an oven. The dried material was ground into a finely divided particulate, powdered form, to provide a powder mixture comprising about 28% (280 g) of *Saussurea acrophila* Diels and *Saussurea ceratocarpa*, present in equal amounts (about 14% each), and about 72% (720 g) of *Aucklandia lappa* Decne. The powder mixture was soaked in about 99.9% ethanol, as extraction solvent, and homogenized for about 10 minutes to provide a solvent/powder mixture.

The solvent/powder mixture was incubated at room temperature for 4 days. The solvent/powder mixture, after incubation, was filtered twice using vacuum to provide a first filtrate and a first retentate. Ethanol was allowed to evaporate from the first filtrate, or extract solution, at room temperature.

The first filtrate was subjected to re-extraction with a re-extraction solvent of about 99.9% ethanol using a shaking water-bath at about 75° C. for about 6 hours, thereby obtaining a re-extraction mixture of the first filtrate and the re-extraction solvent. The re-extraction mixture was filtered, thereby obtaining a second filtrate, or extract solution, and a second retentate. Ethanol was allowed to evaporate from the second filtrate at room temperature.

The yield of this two-step extraction method provided a filtered herbal extract. The filtered herbal extract was yellowish brown.

The filtered herbal extract was kept at about 4° C. The concentration of this filtered herbal extract was adjusted accordingly, e.g. about 800 g thereof was added to one liter of distilled water.

Example 2

Toxicity Testing

Two different species of animals were the subjects of the experiment: rabbits (group-A) and WKY rats (group-B). The animals were obtained from Small Animal House, SQU, Oman. Group-A Rabbits, included ten (10) male rabbits and five (5) female rabbits, each weighing between 800 g to 1300 g. Group-B WKY rats included nine (9) males and six (6) females, each weighing between 300 g to 600 g. Both rabbits and rats were randomly divided to investigate the lethal dosage.

The filtered herbal extract, prepared as described in Example 1, was administered orally to the animals using antistatic at variable dosages to reach a maximum of about 16 g/Kg for each animal group. The concentration of each dose of fluid containing the filtered herbal extract was about 1 g/ml. Accordingly, the higher dosage group at 15 g/Kg had a concentration of about 5 ml of 15 g/Kg, which could be calibrated to suit bigger animals, including humans.

The animals were observed for behavior continuously for a period of two weeks after administration. Observation was conducted hourly at day 1; and during the following days, observation was conducted four to six (4-6) times per day. At the end of the observation period, animals were sacrificed and dissected to examine the eyes, liver, lung, and spleen for any adverse effects.

A separate experiment was performed in parallel to the above animal groups where, a medicament of camel's milk as described below, was also given to each group of animals to evaluate the toxicity status thereof. The volume of the medicament of camel's milk was given according to the animal's capacity on a daily basis for a period of two weeks.

No abnormal behavior was observed in either groups of animals during the observation period. All animals were alive after the two weeks of having been given 16 g/Kg or the medicament of camel's milk. All animals showed normal body weight increase during the two weeks period. Biochemical analysis showed normal range of ALT, AST, CBC, and GGT. Inspection of the eyes, liver, lung, and spleen (after scarification and dissection) showed no extraordinary signs. The results when compared to a general acute toxicity index were normal and no acute toxicity was observed. Based on the results of the toxicity experiment, the weight range of the filtered herbal extract or diffused composition (i.e. a mixture, or solution, of the composition of the extract in water) is preferred to be 10-20 g/Kg of animal weight for each extract.

In the tables below, "composition" means the filtered herbal extract described in Example 1, on a dry mass basis dissolved in distilled water at about 973.5 g/5000 ml.

TABLE 1

Rabbits Received 16 g/Kg Orally

| Rabbit No. | Weight (Kg) | Dose in grams | Dose in mL |
|---|---|---|---|
| 1 | 0.8 | 12.8 | 68.2 |
| 2 | 1.4 | 22.4 | 119.4 |
| 3 | 1.5 | 24 | 127.9 |
| 4 | 1.15 | 18.4 | 98.1 |
| 5 | 1.05 | 16.8 | 89.5 |
| 6 | 1 | 16 | 85.3 |
| 7 | 1.15 | 18.4 | 98.1 |
| 8 | 1 | 16 | 85.3 |
| 9 | 1.3 | 20.8 | 110.9 |
| 10 | 0.9 | 14.4 | 76.8 |

TABLE 2

WKY Rats Received 16 g/Kg Orally

| Rat No. | Weight (Kg) | Dose in grams | Dose in mL |
|---|---|---|---|
| 1 | 0.3 | 4.8 | 25.6 |
| 2 | 0.25 | 4 | 21.3 |
| 3 | 0.25 | 4 | 21.3 |
| 4 | 0.4 | 6.4 | 34.1 |
| 5 | 0.25 | 4 | 21.3 |
| 6 | 0.3 | 4.8 | 25.6 |
| 7 | 0.25 | 4 | 21.3 |
| 8 | 0.25 | 4 | 21.3 |
| 9 | 0.5 | 8 | 42.6 |
| 10 | 0.5 | 8 | 42.6 |

Example 3

Developing Modified HIV Provirus Plasmids

For generation of anti-mouse HIV antibody, conventional immunization was performed in parallel with DNA immunization using fifty (50) Balb-C mice. Mice were boosted 3 times at 2 weeks interval. Blood was collected before and after boosting for seropositivity analysis using ELISA kit.

For generation of anti-camel HIV antibody, conventional immunization was performed in parallel with DNA immunization using female camels. Each camel was boosted 6 times at two week intervals, using different delivery routes.

Blood was collected before and after boosting for seropositivity analysis using ELISA kit.

For analysis of the generated anti-HIV camel antibodies, anti-HIV camel antibodies secreted in the camel milk and orally taken by HIV/AIDS patients was analyzed. Assessment of the impact of the treatment modality, virus load, and $CD4^+T$ cell count of HIV/AIDS patients was made for three months.

Both HIV/pwT/Bal vector (SEQ ID NO.:2) and HIV/pNL/4-3 vector (SEQ ID NO.:1), were donated from the NIH-AIDS Research and Reference Reagent Program, USA. Prior to the amplification step, both vectors' DNA insets were modified using techniques generally known in the art. All experiments were performed using the modified vectors "HIV/pwT/Bal/Mod" and "HIV/pNL/4-3/Mod" (corresponding to SEQ ID NO.:3 and SEQ ID NO.:4, respectively). Transformed "one shot chemically competent" *E. coli* colonies were amplified in about 500 ml LB cultures and the plasmid DNA constructs were purified chromatographically using Qiagen Megaprep kits, according to manufacturer's instructions (MegaPrep; Qiagen, Hilden, Germany). The purified DNA was stored at −20° C. until ready for use.

Before proceeding to DNA immunization, the ability of the HIV/pwT/Bal/Mod vector (SEQ ID NO.:3) and HIV/pNL/4-3/Mod vector (SEQ ID NO.:4) to express recombinant HIV Provirus was confirmed in vitro by transfection of mammalian COS-7 and 293 T cells (ATCCC, Germany) with DNA or vector vaccines alone (Control plasmids lacked the HIV inserts). The main reagents used in this transfection/expression procedure were FUGENE 6 (Roche) and/or Lipofectamine 2000 (Invitrogen, CA). The transfection procedure was performed according to manufacturer instructions.

Monitoring of virus production was performed every 2 days by measuring p24 antigen concentration in the culture fluid starting on day 5 using the p24 antigen ELISA kit. Culture medium was changed fully and regularly every two days after day 5 when completing the p24 antigen measurement. Three or more harvests were performed when the p24 concentration reached greater than about 10 ng p24 per milliliter. Each harvested culture fluid sample was saved, filtered through a 0.45-μm pore filter, and treated with about 50 units of Benzonase per ml of filtered HIV viral stock for about 25 minutes at about 37° C. to remove contaminating plasmid DNA. Previous studies proposed that the use of Benzonase has no impact on the viral ability to infect or to bind to its specific targets, and therefore any effect of Benzonase on infectivity would be only slight. Virus stocks were frozen at −80° C. to halt Benzonase activity and/or until use.

Viral titers were calculated using the TCID50 assay, according to the method of Reed and Muench (1938). Samples with less than about 0.2 ng p24/ml were considered negative for the calculation.

Example 4

HIV Provirus Immunization in BALB/c Mice

Female BALB/c Mice [a total of 10 mice] were immunized by intramuscular injection with about $1.0 \times 10^8$ infection units (equivalent to $1 \times 10^6$ TCID50 of concentrated vector stocks) of HIV recombinant viruses over a time course of 4 weeks post-immunization and boosted 1 month later with the same dose of recombinant viruses. The control group (a total of 10 BALB/c mice), were immunized with the same dose but with vectors alone. For seroconversion analysis, blood samples were collected via the periorbital route 4 weeks after the first inoculation, then at 4 weeks after boosting.

Example 5

DNA Immunization of BALB/c Mice

The HIV/pwT/Bal/Mod (SEQ ID NO.:3) and HIV/pNL/4-3/Mod (SEQ ID NO.:4) vectors and the control pwT/Bal and pNL/4-3 plasmids were precipitated onto 1.6 μm gold beads and loaded into half-inch lengths of plastic tubing according to the manufacturer's instructions (BioRad, Hercules, Calif.). The amount of gold powder and DNA were acclimated to give pieces of tubing ('shots') containing 1 mg DNA/0.5 mg gold. The abdomens of thirty anaesthetized, 8±10-week-old female BALB/c were shaved and subjected to three 'shots' expelled under a burst of helium gas at about 350 psi into the epidermal layer using the Helios GeneGun (BioRad). Mice were divided into three groups of 10 mice in each group, immunized with about 3 mg of the HIV/pwT/Bal/Mod (SEQ ID NO.:3) and HIV/pNL/4-3/Mod (SEQ ID NO.:4) DNA constructs or the vectors alone, on three occasions, two weeks apart and their sera were examined four weeks later.

For each of the HIV/pwT/Bal/Mod (SEQ ID NO.:3) and HIV/pNL/4-3/Mod (SEQ ID NO.:4) DNA constructs and the empty plasmids vectors, about 0.5 mg of each in saline was adjusted to about 100 μg with distilled water and about 25 μl was injected into each rectus femoris muscle of 30 8±10-week-old female BALB/c mice with a 25 gauge needle on three occasions, two weeks apart. Clinical parameters for each animal were inspected, including weight of animals, temperature and swelling of lymph nodes. Blood samples were drawn prior to each vaccination, then at week six and week eight. The immunization sites were examined for any adverse reactions.

Evaluation of antibody seroconversion was conducted using ELISA. Ninety-six-well plates (ICN, Costa Mesa, Calif.) coated with recombinant gp140 (0.5-1 μg/ml in PBS) or gp120 (1 μg/ml) in 0.05 M carbonate were buffered overnight at 4° C. The plates were washed 3 times with TST (Tris (0'01 m, pH 8.5), saline (NaCl, 0.15 m) and Tween 20 (0.1%)) and blocked for 1 hour with 5% fat-free dried milk (Carnation, Wirral, UK) in TST at 37° C. Individual sera from all inoculated BALB/c mice, including the control groups, were diluted 1:500 with 5% milk and applied, in duplicate, to the plates overnight at 4° C. The plates were washed 3 times with TST and horseradish peroxidase-(HRP)-conjugated anti-mouse immunoglobulin reagents (Nordic, Tilburg, The Netherlands), diluted to 1:1000 with TST, and then added for 2 hours at 37° C. The plates were washed 3 times and the assay developed with a 0.02% solution of the chromogenic substrate 2,2'-azino-bis (2-ethylbenzthiazoline-6-sulphonic acid; Sigma, Poole, UK) in phosphate-citrate buffer (pH 4.0) containing 0.015% hydrogen peroxide and the optical density (OD) were read at 405 nm.

Immunoblotting results were analyzed using one and two-dimensional SDS-PAGE immunoblotting assay. Western blot or protein immunoblot from the above gels were used to transfer HIV fractionated recombinant proteins to nitrocellulose and molecular weight markers visualized by reversible staining with Ponceau S.

The filters were blocked with 5% non-fat milk for 1 hour at room temperature, washed 3 times with TST and diluted (5% milk) sera are added overnight at 4° C. The filters were washed 3 times with TST and incubated for 2 hours at room temperature with HRP- or alkaline phosphatase-conjugated goat anti-mouse IgG, or anti-rabbit IgG (1:1000; Sigma Aldrich). Unbound secondary antibody was washed off and the specific antigen-bound antibody was visualized with the appropriate substrate solution.

Seroconversion of the anti-HIV antibodies was confirmed. DNA immunization with the HIV Provirus DNA constructs was found to generate higher titer seroconversion than immunization with the recombinant HIV Provirus of Example 4.

Example 6

Generation of Anti-HIV Camel Antibodies

The methods for DNA immunization of Example 5 were followed to immunize female camels with slight modifications based on the vector/recombinant HIV Provirus and the period of immunization. Seven female well-milking camels (healthy and infection free, as checked by veterinary doctor) were used. The first 5 camels were immunized with about 10 mg each of the HIV/pwT/Bal/Mod (SEQ ID NO. 3) and HIV/pNL/4-3/Mod DNA (SEQ ID NO.: 4) constructs, using the GeneGun protocol, on six occasions, two weeks apart. Their sera and milk were then examined 12 weeks later. The same group was further injected "i.m." with 1 ml of both the HIV/pwT/Bal/Mod (SEQ ID NO. 3) and HIV/pNL/4-3/Mod DNA (SEQ ID NO. 4) constructs adjusted to about 20 mg in distilled water, into each rectus femoris muscle of the same camel with an 18 gauge needle. The same camels were used for the two routes to emphasize the delivery intake of the vector/DNA constructs and to initiate different orientation of the Th1 and Th2 immune responses. The second group comprising the last two female camels was non-immunized and used as a control group.

Confirmation of seroconversion of the anti-HIV camelid antibodies was analyzed in the same manner as in Example 5. HIV neutralization assays were also performed as described below (prior to performing the clinical trial) as an efficacy procedure of the generated anti-HIV camelid antibodies. Both the camel serum and camel milk were used for these analyses. Furthermore, techniques generally known in the art were used to generate a secondary antibody against the generated anti-HIV camel IgG antibodies (for use in the ELISA and immunoblotting assays, conjugated with a proper substrate such as HRP). The secondary antibody was generated by using serum from an unimmunized camel to immunize a goat, and isolating the goat anti-camel antibodies.

Example 7

Sero-Neutralization

In vitro HIV neutralization assessment was performed using the indicator cell line HEK293T. Briefly, HEK293T cells were seeded into 24-well plates (20,000 cells per well) and incubated for 24 hours at 37° C. in DMEM-10% FCS supplemented with hygromycin plus G418 to select and maintain the eukaryotic cells. Culture medium was changed with 30 µl of DMEM-10% FCS-DEAE Dextran (10 µg/ml) and cells were then incubated further for 30 minutes at 37° C. HIV Provirus (about 0.5 ng per well) was then incubated with 1:30 diluted camel milk and/or sera in 30 µl of FCS-free culture medium at 37° C. for 45 minutes and the mixtures virus-sera/milk were added to the cells in duplicate. Two hours later 100 µl of DMEM-10% FCS was added to each well. Subsequently wells were incubated for 48 hours and then β-galactosidase activity was measured using a chemiluminescent reporter gene assay (Roche). The mean neutralization for milk and sera tested were compared and reported to the value recorded in wells of the control containing serum of non-immunized camel at the same dilution that served as reference for 100% infection.

These tests confirmed that (i) DNA immunization is the most efficient DNA-delivery route in contrast with the recombinant HIV immunization and (ii) also showed that satisfactory anti-HIV titers are only achieved after the final immunization. The generated anti-HIV antibodies were found to be significant and showed 100% efficacy to neutralize the HIV Provirus.

Example 8

Clinical Testing

Seventeen (17) patients of Arab, Indian and African origin [excluding +Ve and −Ve controls] were studied and followed up for six months [two months of which are under the invented therapy]: Patients were excluded if they had administered any investigational drug less than 6 weeks prior to the first dose of the medicament of the invention. The selected patients had never been prescribed any HIV/AIDS drugs. Patients' immune function was abnormal (i.e., the $CD4^+$ cells to $CD8^+$ cells ratio is under 1, the number of $CD4^+$ T cells is under $200/mm^3$). The average age of each patient is above 16 years. No pregnant women were chosen. The patients agreed voluntarily to use the medicament of the invention.

Patients were required to take an ELISA test to indicate the presence of the HIV virus. Patients underwent testing with monoclonal antibody reagent and flow cytometry (FAC-SCAN) before and subsequently every two, four weeks and then after two and six months and after treatment ceased to calculate the rate of $CD4^+$ to $CD8^+$ cells, and the quantity of $CD4^+$ cells (in $cm^3$) as index to measure the immune function of patients under the treatment. Complete diagnostic records were recorded, including physical sign and pulse condition.

The criteria for measuring curative effect were: if testing PCR and/or RT-PCR is negative, the immune function increased and/or recovers to normal (i.e., ratio of $CD4^+$ to $CD8^+>1$ and/or the percentage of the $CD4^+$ T cells are increased in correlation to the total WBC, and if there are no symptoms, no physical signs and no opportunistic infections. The criteria for measuring evident effect were: if HIV appears negative or undetectable, the immune function improved dramatically (i.e., ratio of $CD4^+$ and $CD8^+>0.2$ but the number of $CD4^+$ T cells is $\geq 200/mm^3$), if opportunistic infections were basically removed (disappeared) and the symptoms and physical signs recovered fundamentally back to normal. The criteria for measuring some effect were: if testing PCR for HIV appeared positive, the immune function improved (ratio $CD4^+$ to $CD8^+>0.2$, the quantity of $CD4^+$ T cells is beyond $40/mm^3$), opportunistic infections improved and the symptoms and physical signs were relieved. The criteria for measuring no effect were: if there were no dramatic changes to the index of immune function, or if there was a decrease of immune function in the treatment.

A comprehensive analysis of the curative effect according to the clinical symptoms and immune state before and after treatment are studied and recoded. The total number of patients was 17 (4 females and 13 males). Their infection was confirmed by both ELISA and Quantitative PCR. The average age was about 33 years, with the oldest being 55 years old, and the youngest being 24 years old.

Pretreatment status was determined by physical examination. All patients showed common symptoms of depression, weakness, stegnosis and weight loss associated with loss of appetite, and some patients occasionally developed fever.

In accordance with the present techniques, camel's milk was used from a camel which had been DNA immunized against HIV and which had ingested, via intubation, the filtered herbal extract of Example 1. The immunized camel's milk from these camels was the only source of treatment administered to the patients. Each patient consumed about 300 ml of the immunized milk three times a day on a daily basis. Immunized milk was administered until HIV viral load was undetected for two-tested occasions or when a –Ve viral load was shown. Patients were then asked to stop taking the medicament of the invention for 16 weeks and were tested for HIV from the start of the 16 week period. Two patients "as control group 1" were administered the same dose of milk but from an unimmunized camel with no intake of the composition of the invention.

Detailed hematological and biochemical tests were conducted on each patient. Table 2 shows the most significant clinical data obtained from the pilot studies on the effectiveness of the herbal composition and camel milk in protecting HIV/AIDS patients from the debilitating effects of the disease.

Ten (10) ml blood samples were taken from the patients each time before, during, and after the treatment and further tested using ELISA, Viral Load (VL), $CD4^+$ cells, $CD8^+$ cells, White Blood cells (WBC) and other screening profile such as full blood count (FBC), liver function, renal function, fasting lipid profile, blood glucose. Moreover, physical examination including recording weight, was performed each time before, during, and after the treatment.

Of the 17 patients, the mean $CD4^+/CD8^+$ ratio (ratio of helper T cells to cytotoxic T cells) at the commencement of treatment was 0.42±0.05 (the ratio in a healthy population is 1.0-3.5). After a treatment period ranging from 2-8 weeks the $CD4^+/CD8^+$ cells ratio had significantly increased by over two-fold to 0.90±0.02 ($p<0.001$). Concurrently with this change, an improvement in the response to skin hypersensitivity tests and a general increase in well-being were observed. This latter effect is demonstrated by the overall restoration of body weight, an increasing average from 67.9 to 88.1 Kg, a weight gain of 10 Kg ($p<0.003$).

Table 3 shows the percentage elevation in the $CD4^+$ T cell populations of peripheral blood cells from HIV infected patients upon receiving the immunized camel's milk within the period of 2 months. It also shows the $CD4^+$ T cells after 6 months from which patients stopped the treatment. The $CD4^+$ percentages reported in Table 3 represent the percentage of white blood cells that are $CD4^+$ cells. For HIV negative adults, the average $CD4^+$ percentage is about 45% (This can range from 24% to 64%). In adults, a $CD4^+$ percentage of about 12%-15% is considered similar to a $CD4^+$ count of 200 cells/$mm^3$. A percentage of about 15%-20% is considered similar to an absolute $CD4^+$ cell count of 300 cells/$mm^3$. Missing data points were due to patients lacking the financial means to travel to the checkup location (Sana'a City in the Republic of Yemen).

Table 4 shows the elevation in the Total White Blood Cells population of peripheral blood from HIV infected patients upon receiving the immunized camel's milk within the period of 2 months. The data reported in Table 4 represents the total white blood cells per cubic millimeter ($mm^3$). Normal white blood cell counts of healthy adults are within the range of about 5,000-10,000 $mm^3$. Missing data points were again due to patients lacking the financial means to travel to the checkup location (Sana'a City in the Republic of Yemen).

Table 5 shows the monitoring of "HIV Viral Load" throughout the treatment period. Moreover, it also illustrates the screening profile of the patients' viral load after 6 months from which patients stopped the treatment. Viral load is reported as copies of HIV in one cubic millimeter of blood.

TABLE 3

$CD4^+$ T Cell Populations in Peripheral Blood

|  | P1f | P2f | P3f | P4f | P5m | P6m | P7m | P8m | P9m | P10m | P11m | P12m | P13m | P14m | P15m | P16m | P17m | Pc1m | Pc2m | Pc1f | Pc2f |
|---|---|---|---|---|---|---|---|---|---|---|---|---|---|---|---|---|---|---|---|---|---|
| Pre | 38 | 19 | 31 | 8 | 8 | 21 | 42 | 41 | 31 | 34 | 36 | 29 | 31 | 49 | 22 | 19 | 13 | 11 | 22 | 23 | 19 |
| 2 Wks | 27 | 10 | 23 | 3 | 3 | 11 | 21 | 32 | 24 | 18 | 28 | 17 | 22 | 26 | 11 | 16 | 6 |  |  |  |  |
| 4 Wks | 39 | 21 | 26 | 11 | 11 | 23 | 38 | 28 | 42 | 39 | 31 | 11 | 15 | 32 | 17 | 21 | 19 |  |  |  |  |
| 2 M | 53 | 48 | 43 | 36 | 36 | 23* | 61 | 39 | 55 | 50 | 37 | 32 | 47 | 63 | 36 | 29 | 25 | 13 | 19 | 22 | 23 |
| 6 M | 43 | 39 | 31 | 29 | 29 |  |  |  |  |  |  |  | 29 |  |  |  | 30 |  |  |  |  |

P = patient;
1-17 = patient number;
m = male;
f = female;
c = control;
*Patient experienced diarrhea and had a sexual relationship with an infected individual during the course of treatment.

TABLE 4

Total White Blood Cells in Peripheral Blood (In Thousands)

|  | P1f | P2f | P3f | P4f | P5m | P6m | P7m | P8m | P9m | P10m | P11m | P12m | P13m | P14m | P15m | P16m | P17m | Pc1m | Pc2m | Pc1f | Pc2f |
|---|---|---|---|---|---|---|---|---|---|---|---|---|---|---|---|---|---|---|---|---|---|
| Pre | 2.7 | 3.5 | 4.0 | 5.2 | 2.8 | 1.953 | 2.7 | 3.1 | 4.1 | 0.82 | 3.6 | 1.953 | 2.08 | 3.1 | 2.7 | 3.1 | 4.1 | 3.25 | 2.89 | 3.1 | 3.2 |
| 2 Wks | 2.6 | 3.4 | 3.3 | 5.4 | 3.2 | 1.88 | 2.3 | 5.7 | 5.1 | 2.04 | 4.0 | 1.88 | 1.984 | 3.0 | 2.3 | 5.7 | 5.1 |  |  |  |  |
| 4 Wks | 2.8 | 4.3 | 3.4 | 5.9 | 3.8 | 0.82 | 1.01 | 6.1 | 5.8 | 1.96 | 4.4 | 2.89 | 3.4 | 2.66 | 1.01 | 6.1 | 5.8 |  |  |  |  |

TABLE 4-continued

Total White Blood Cells in Peripheral Blood (In Thousands)

| | P1f | P2f | P3f | P4f | P5m | P6m | P7m | P8m | P9m | P10m | P11m | P12m | P13m | P14m | P15m | P16m | P17m | Pc1m | Pc2m | Pc1f | Pc2f |
|---|---|---|---|---|---|---|---|---|---|---|---|---|---|---|---|---|---|---|---|---|---|
| 2 M | 3.5 | 6.8 | 5.1 | 6.5 | 3.95 | 1.01* | 3.0 | 8.322 | 5.6 | 3.2 | 3.9 | 3.981 | 3.9 | 3.45 | 3.2 | 4.5 | 6.366 | 3.0 | 3.143 | 3.5 | 3.01 |
| 6 M | 4.1 | 5.6 | 4.8 | 5.2 | 4.0 | | | | | | | | 4.2 | | | 5.1 | | | | | |

P = patient;
1-17 = patient number;
m = male;
f = female;
c = control;
*Patient experienced diarrhea and had a sexual relationship with an infected individual during the course of treatment.

TABLE 5

HIV Viral Load in Copies per Cubic Milliliter of Blood (In Thousands)

| | 1f | 2f | 3f | 4f | 5m | 6m | 7m | 8m | 9m | 10m | 11m |
|---|---|---|---|---|---|---|---|---|---|---|---|
| Pre | 8.3 | 1.1 | 4.6 | 10.04 | 0.759 | 0.65* | 27 | 19 | 0.72 | 18.0 | 4.0 |
| 2 Wks | 4.1 | 0 | 0.397 | 2.613 | 1.01 | 47.3* | 0 | 2.1 | 1.223 | 18.7 | 5.52 |
| 4 Wks | 0 | 0 | 0 | 0.18 | 2.99 | 18.7* | 0 | 0 | 0 | 0.02 | 0 |
| 2 M | Ve$^-$ | Ve$^-$ | Ve$^-$ | Ve$^-$ | 0 | 0* | Ve$^-$ | Ve$^-$ | Ve$^-$ | Ve$^-$ | Ve$^-$ |
| 6 M | Ve$^-$ | Ve$^-$ | Ve$^-$ | Ve$^-$ | Ve$^-$ | | | | | | |

| | 12m | 13m | 14m | 15m | 16m | 17m | c1m | c2m | c1f | c2f |
|---|---|---|---|---|---|---|---|---|---|---|
| Pre | 219 | 2.5 | 18.7 | 30.3 | 2.5 | 12.5 | 56 | 333 | 10 | 121 |
| 2 Wks | 133 | 10.7 | 15.8 | 37.1 | 0 | 7.6 | | | | |
| 4 Wks | 0 | 0 | 0 | 0 | | 0 | | | | |
| 2 M | Ve$^-$ | Ve$^-$ | 0 | Ve$^-$ | Ve$^-$ | Ve$^-$ | 62 | 320 | 14.3 | 193 |
| 6 M | | Ve$^-$ | | | | Ve$^-$ | | | | |

1-17 = patient number;
m = male;
f = female;
c = control;
*Patient experienced diarrhea and had a sexual relationship with an infected individual during the course of treatment.

All patients regardless of their lifestyle, race, age and sex showed that their case of HIV/AIDS to be improved and 0 cases became worse. According to the criteria of curative effect the 17 cases are effective and 0 cases were ineffective in this study.

No case in the study showed side effects in general, except that namely 1 case felt diarrhea and tired for a short period. All of the other 16 cases continued to take the medicine in the prescribed quantity.

This therapeutic composition was very effective to suppress HIV replication as well as to stimulate its eradication from the blood stream. During the treatment process, all patients had positive response with no side effects, except that namely 1 case felt diarrhea and tired for a short period. However, the symptoms of the patients were noticeably improved after two weeks of the treatment including alleviation of weakness, depression, and stegnosis. The abdominal region pain and uncomfortable feeling also disappeared. Those patients who lost weight had about 10 Kg increase of body weight after two months of treatment. In the treatment, most if not all of the symptoms of the cases showed improvement after taking the HIV-immunized camel's milk. This was also associated with immune function improvement as well as increased in the number of the CD4+ T cells. The HIV-immunized camel's milk for all cases was found to be effective in the eradication of the HIV from the patients' blood streams. This was confirmed after four months after patients stopped taking the medication and were screened by Real Time PCR.

The therapeutic composition was therefore found to be highly effective to quickly decrease HIV viral load, and has the potential to eradicate HIV infection. The therapeutic composition also has the potential to stimulate and increase WBC significantly.

Two similar and independent investigations were performed where two groups of patients were given either (i) the medicament milk from camels intubated with the herb alone (without DNA immunization), or (ii) the medicament milk from camels that had been DNA immunized, but had not been fed the herbal composition. Both of these groups demonstrated reduction of viral load after treatment; however, neither of these experimental groups demonstrated full eradication of the HIV infection, as the virus was detected four months from the time that treatment was stopped (Table 6 & Table 7).

TABLE 6

Camel Milk Medicament from HIV DNA Immunized Camels (viral load in copies per cubic ml blood)

|        | P1m  | P2m  | P3f  | P4m  | P5f  | P6m  | P7m   | Pc1f | Pc2m |
|--------|------|------|------|------|------|------|-------|------|------|
| Pre    | 1200 | 4300 | 1500 | 2100 | 1800 | 700  | 9100  | 1000 | 5600 |
| 2 Wks  | 2100 | 5100 | 9800 | 3400 | 1300 | 390* | 10900 | 1100 | 5200 |
| 4 Wks  | 650  | 1100 | 3100 | 430  | 600  | 50*  | 3200  |      |      |
| 2 M    | 0    | 0    | 100  | 0    | 0    | 2000 | 300   |      |      |
| 6 M    | 2800 | 1200 | 3100 | 3100 | 2800 | 9000 | 43000 | 1400 | 4700 |

1-7 = patient number;
m = male,
f = female,
c = control;
*Patient showed no adherence with the medicament regimen protocol and had a sexual relationship with an infected individual during the course of treatment.

TABLE 7

Camel Intubated with Herbal Extracts Only (viral load in copier per cubic ml blood)

|        | P1f    | P2f    | P3f    | P4m    | P5m   | P6f   | P7f   | P8m    | P9f    | Pc1f   | Pc2m   |
|--------|--------|--------|--------|--------|-------|-------|-------|--------|--------|--------|--------|
| Pre    | 17,000 | 21,000 | 1,200  | 3,200  | 210   | 1,900 | 6,500 | 3,600  | 7,450  | 10,000 | 76,000 |
| 2 Wks  | 3,000  | 3,400  | 250    | 1,800  | 0     | 400   | 590   | 2,000  | 1,800  | 8,700  | 48,000 |
| 4 Wks  | 1,500* | 800**  | 0      | 430    | 0     | 0     | 0     | 210    | 190    |        |        |
| 2 M    |        |        | 0      | 0      | 0     | 0     | 0     | 0      | 0      |        |        |
| 6 M    |        |        | 3,000  | 98,000 | 4,200 | 7,000 | 4,200 | 56,000 | 115000 | 9,400  | 41,000 |

1-9 = patient number;
m = male;
f = female;
c = control;
*Patient withdrawn from the study at week six.
**Patient showed no adherence with the medicament regiment protocol during the second month of the course of treatment.

It is to be understood that the present invention is not limited to the embodiments described above, but encompasses any and all embodiments within the scope of the following claims.

We claim:

1. A method of making a therapeutic composition of camel milk, comprising the steps of:

immunizing a camel against HIV with DNA encoding HIV antigens to provide an HIV-immunized camel, the immunizing comprising 6 immunization treatments, each immunization treatment including administering about 10 mg of DNA encoding HIV antigens to the camel;

preparing an herbal extract comprising the steps of preparing a powdered mixture of the solid material of *Saussurea acrophila* Diels, *Saussurea ceratocarpa*, and *Aucklandia lappa* Decne, soaking the powdered mixture in a first solvent to provide a solvent/powder mixture, incubating the powder/mixture at room temperature, filtering the powder/mixture after incubation to provide a first filtrate and a first retentate, allowing the first solvent to evaporate from the first filtrate, and combining the first filtrate with a second solvent to provide a re-extraction mixture, filtering the re-extraction mixture to provide an extract solution and a second retentate, and allowing the second solvent to evaporate from the extract solution to provide the herbal extract, the herbal extract comprising about 14% extract of *Saussurea acrophila* Diels, about 14% extract of *Saussurea ceratocarpa*, and about 72% extract of *Aucklandia lappa* Decne;

intubating the HIV-immunized camel with the herbal extract in an amount of 500 g to 800 g of the herbal extract per day; and then collecting an HIV-immunized camel milk from the immunized camel intubated with the herbal extract, the HIV-immunized camel milk including anti-HIV heavy chain IgG antibodies, the HIV-immunized camel milk providing the therapeutic composition.

2. The method of making a therapeutic composition of camel milk according to claim 1, wherein the step of intubating the immunized camel, comprises intubating the immunized camel with about 800 g of the herbal extract per day.

3. A therapeutic composition of camel's milk, comprising: anti-HIV heavy chain IgG antibodies, the therapeutic composition prepared according to the method of claim 1.

4. The method of making a therapeutic composition of camel milk according to claim 1, wherein the first solvent and the second solvent are ethanol.

5. The method of making a therapeutic composition of camel milk according to claim 4, wherein the combining the first filtrate with the solvent comprises using a shaking water bath at 75° C. for 6 hours.

6. The method of making a therapeutic composition of camel milk according to claim 5, wherein the powder/mixture is incubated at room temperature for four days.

* * * * *